(12) United States Patent
Wang et al.

(10) Patent No.: US 9,987,379 B2
(45) Date of Patent: Jun. 5, 2018

(54) MOLECULAR PROBES FOR IMAGING OF MYELIN

(75) Inventors: Yanming Wang, Beachwood, OH (US); Chunying Wu, Mayfield Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 494 days.

(21) Appl. No.: 13/121,742

(22) PCT Filed: Sep. 30, 2009

(86) PCT No.: PCT/US2009/059001
§ 371 (c)(1),
(2), (4) Date: Mar. 30, 2011

(87) PCT Pub. No.: WO2010/039815
PCT Pub. Date: Apr. 8, 2010

(65) Prior Publication Data
US 2011/0189090 A1 Aug. 4, 2011

Related U.S. Application Data

(60) Provisional application No. 61/101,299, filed on Sep. 30, 2008.

(51) Int. Cl.
| | |
|---|---|
| A61K 51/00 | (2006.01) |
| A61K 49/08 | (2006.01) |
| A61K 49/00 | (2006.01) |
| A61K 49/10 | (2006.01) |
| A61K 51/04 | (2006.01) |
| G01N 33/92 | (2006.01) |

(52) U.S. Cl.
CPC ........ *A61K 49/085* (2013.01); *A61K 49/0021* (2013.01); *A61K 49/0032* (2013.01); *A61K 49/0052* (2013.01); *A61K 49/10* (2013.01); *A61K 51/04* (2013.01); *G01N 33/92* (2013.01); *G01N 2405/10* (2013.01); *G01N 2800/285* (2013.01)

(58) Field of Classification Search
CPC .............. A61K 49/085; A61K 49/0021; A61K 49/0032; A61K 49/0052; A61K 49/10; A61K 51/02
USPC ....................................................... 424/1.65
See application file for complete search history.

(56) References Cited

U.S. PATENT DOCUMENTS

| | | | |
|---|---|---|---|
| 5,851,785 A | 12/1998 | Aoyama et al. | |
| 2003/0149250 A1* | 8/2003 | Kung et al. | 534/14 |
| 2004/0131545 A1* | 7/2004 | Kung et al. | 424/1.65 |

| | | | |
|---|---|---|---|
| 2006/0073541 A1 | 4/2006 | Kilgore | |
| 2006/0223141 A1 | 10/2006 | Carey et al. | |
| 2007/0249180 A1 | 10/2007 | Tour et al. | |
| 2008/0253967 A1 | 10/2008 | Kung | |
| 2010/0172836 A1 | 7/2010 | Benedum et al. | |

FOREIGN PATENT DOCUMENTS

| | | | |
|---|---|---|---|
| EP | 1815872 A1 * | 8/2007 | |
| WO | 1994/14477 A1 | 7/1994 | |
| WO | 1996/31206 A2 | 10/1996 | |
| WO | 1996/31206 A3 | 10/1996 | |
| WO | 2003/018070 A1 | 3/2003 | |
| WO | WO 2008/128129 A1 | 10/2008 | |

OTHER PUBLICATIONS

Risdale et al. J. Biol. Chem. 272, 7, 4269-4275.*
Kornblum et al. J. Clin. Pharmacol. 2001 41: 55S.*
Wu et al. J. Histochem.Cytochem. 2006, 54m 997-1004.*
Jacobs et al. Curr. Opin. Neurobiol. 2001, 11, 621-629.*
Stankoff, et al., "Imaging of CNS myelin by positronemission tomography", PNAS vol. 103 No. 24, 9304-9304, Jun. 13, 2006.
Wu, Chunying, et al., "Lipophilic Analogs of Thioflavin S as Novel Amyloid-Imaging Agents", Current Alzheimer Research, 2006, 3, 259-266.
Wu, Chunying, et al., "Dibenzothiazoles as novel amyloid-imaging agents", Bioorganic & Medicinal Chemistry 15 (2007) 2789-2796.
Extended European Search Report dated Jun. 8, 2015.
Xiangji Chen "QSAR and primary docking studies of trans-stilbene (TSB) series of imaging agents for B-amyloid plaques", Journal of Molecular Structure: THEOCHEM 763 (2006) 83-89.
Chunying Wu, et al. "A Novel Fluorescent Probe That Is Brain Permeable and Selectively Binds to Myelin", Journal of Histochemistry & Cytochemistry, vol. 54(9): 997-1004, 2006.
Chunying Wu, et al. "Molecular Probes for Imaging Myelinated White Matter in CNS", J. Med. Chem. 2008, 51, 6682-6688.
Changning Wang et al. "Design, Synthesis, and Evaluation of Coumarin-Based Molecular Probes for Imaging of Myelination", J. Med. Chem. 2011, 54, 2331-2340.
Luca Frullano et al. "A Myelin-Specific Contrast Agent for Magnetic Resonance Imaging of Myelination", Journal of the American Chemical Society 2011, 133, 1611-1613.
Changning Wang et al. "In Situ Fluorescence Imaging of Myelination" Journal of Histochemistry & Cytochemistry, vol. 58(7): 611-621, 2010.

* cited by examiner

*Primary Examiner* — Michael G Hartley
*Assistant Examiner* — Sean R Donohue
(74) *Attorney, Agent, or Firm* — Tarolli, Sundheim, Covell & Tummino LLP

(57) ABSTRACT

A molecular probe for labeling myelin includes a fluorescent trans-stilbene derivative.

9 Claims, 13 Drawing Sheets

Compound 3   Compound 6   Compound 7

*magnification: upper panel (cc), X20; lower panel (cb), X10*

Compound 6

Compound 7

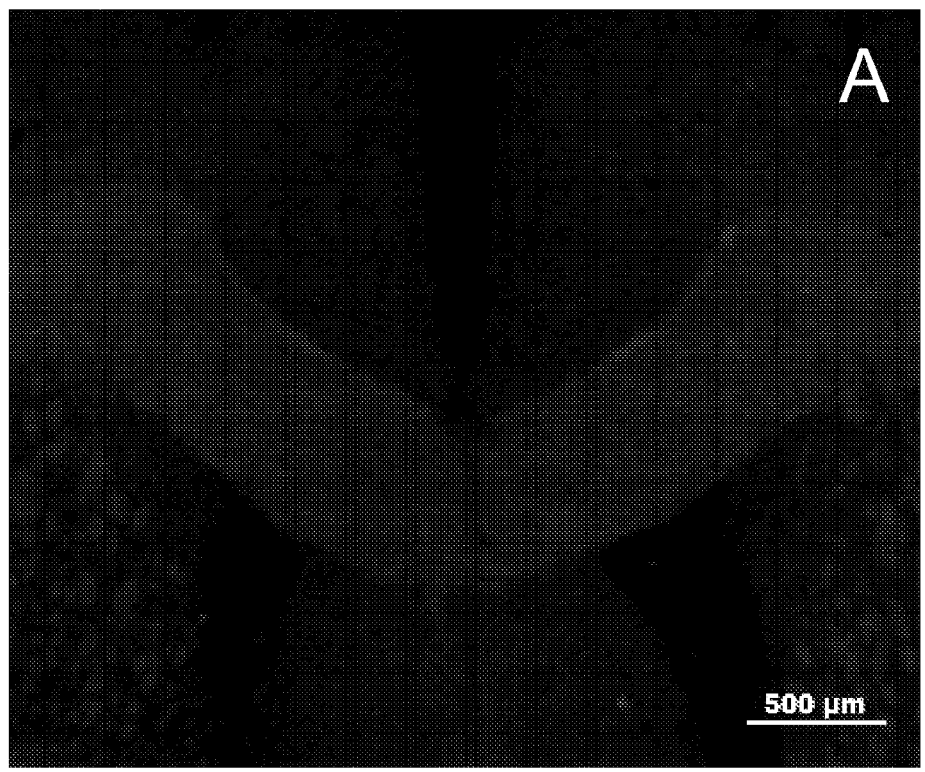
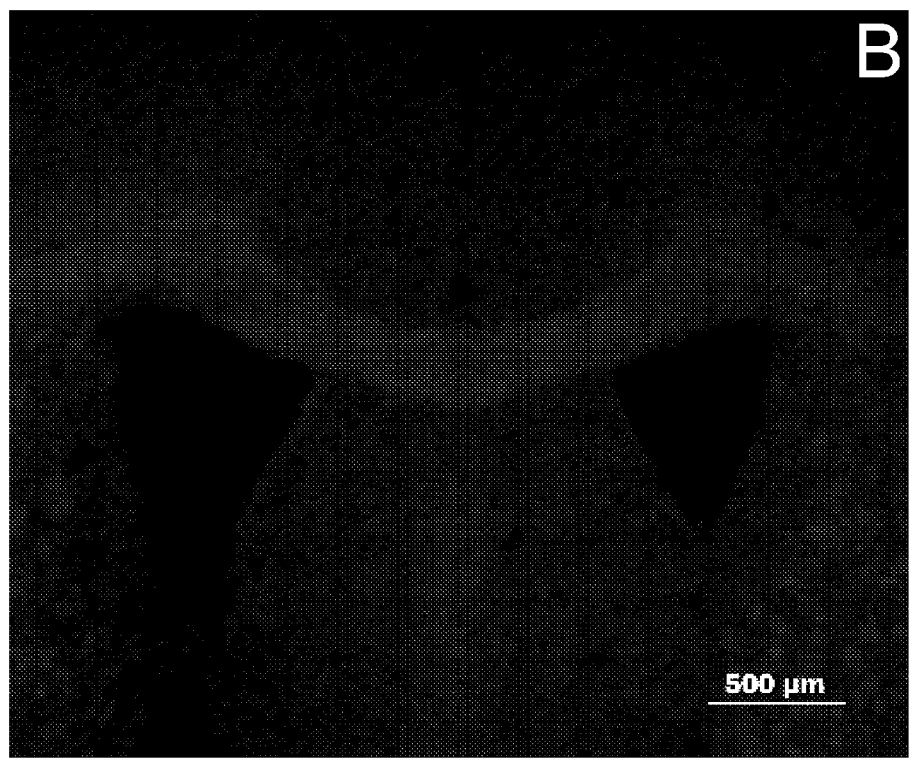
Fig. 12A-B

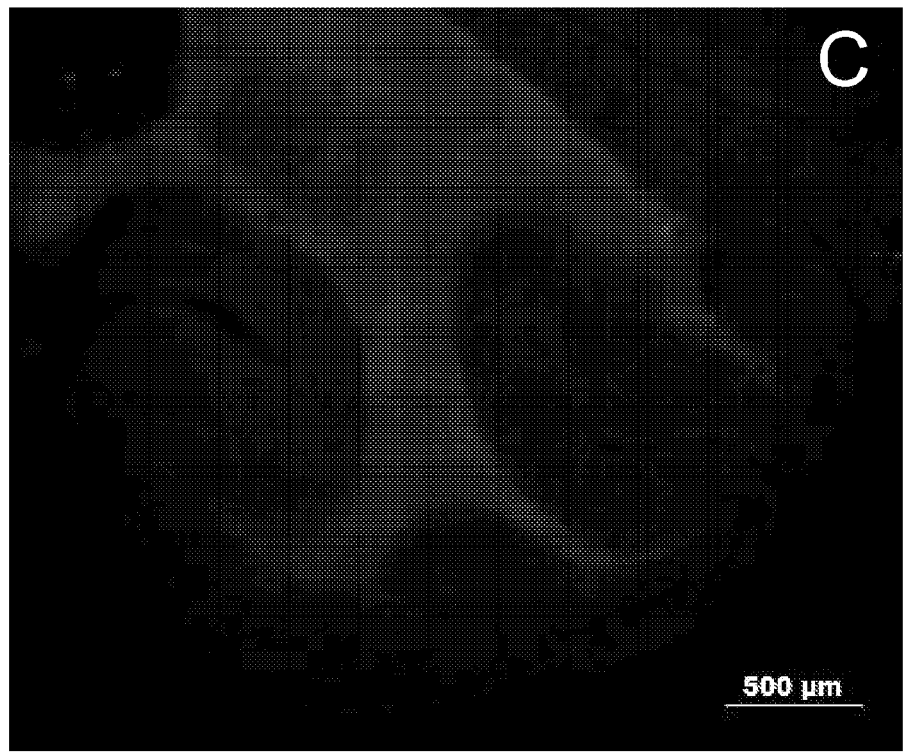
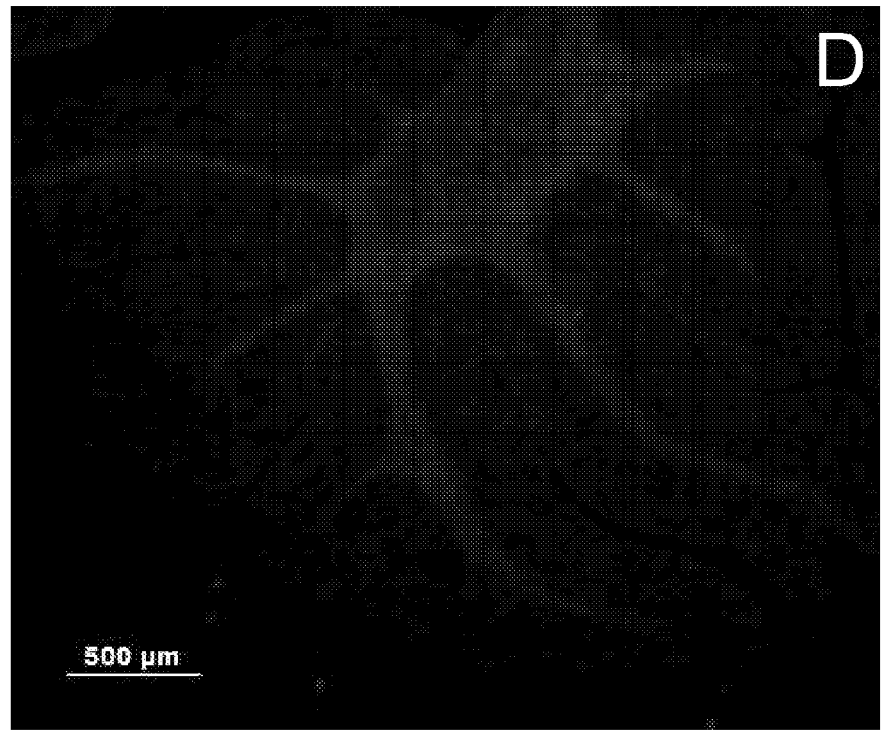
Fig. 12-C-D

SEQUENCE LISTING

<160> NUMBER OF SEQ ID NOS: 2

<210> SEQ ID NO 1
<211> LENGTH: 18
<212> TYPE: DNA
<213> ORGANISM: Mus musculus

<400> SEQUENCE: 1
gcagtggacc acggtcat                                                 18

<210> SEQ ID NO 2
<211> LENGTH: 20
<212> TYPE: DNA
<213> ORGANISM: Mus musculus

<400> SEQUENCE: 2
ctggcaacta gaaggcacag                                               20

MOLECULAR PROBES FOR IMAGING OF MYELIN

RELATED APPLICATION

This application is corresponds to PCT/US2009/059001, filed Sep. 30, 2009, which claims the benefit of U.S. Provisional Application No. 61/101,299, filed Sep. 30, 2008, the subject matter, of which is incorporated herein by reference in their entirety.

GOVERNMENT FUNDING

This invention was made with government support under Grant No. R01 NS061837 awarded by The National Institutes of Health and National Multiple Sclerosis Society. The United States Government has certain rights in the invention.

TECHNICAL FIELD

The present invention relates to molecular probes and to methods of their use, and particularly relates to molecular probes that readily enter the brain and selectively localize in the myelinated regions.

BACKGROUND OF THE INVENTION

Myelin is a specialized membrane that ensheathes neuronal axons, promoting efficient nerve impulse transmission (Morell and Quarles (1999) Basic Neurochemistry: molecular, cellular, and medical aspects. In Siegel G J, ed. Myelin Formation, Structure, and Biochemistry. Lippincott-Raven Publishers, 79-83). Due to its important biological functions in the normal central nervous system (CNS) and its vulnerability in disease, several techniques have been developed to visualize and characterize myelin histopathology. These can be broadly divided into those based upon antibody immunohistochemistry (IHC) (Horton and Hocking (1997) Cereb. Cortex 7:166-177) and more traditional histochemical procedures. The classic histochemical stains include luxol fast blue MBN (Kluver and Barrera (1953) J Neurosci Methods 153: 135-146; Presnell and Schreibman (1997) Humanson's Animal Tissue Techniques, 5$^{th}$ ed.; Kiernan (1999) Histological and Histochemical Methods: Theory and practice, 3$^{rd}$ ed.; Bancroft and Gamble (2002), Theory and Practice of Histological Techniques, 5 ed. and Sudan Black B (Lison and Dagnelie (1935) Bull. d'Histologie Appliquee 12: 85-91). Traditional chromogenic methods also include the Palweigert method ((Weigert (1884) Fortschr Deutsch Med 2: 190-192, (1885) Fortschr Deutsch Med 3:236-239; Clark and Ward (1934) Stain Technol 54:13-16), the Weil stain (Weil (1928) Arch Neurol Psychiatry 20:392-393; Berube et al. (1965) Stain Technol 40:53-62)), the Loyez method (Cook (1974) Manual of Histological Demonstration Methods, 5$^{th}$ ed.), and a method based on horse serum followed by subsequent reaction with diaminobenzidine (McNally and Peters (1998) J Histochem Cytochem 46:541-545). In addition, modified silver stains including the Gallyas method (Pistorio et al. (2005) J Neurosci Methods 153: 135-146) and Schmued's gold chloride technique (Schmued and Slikker (1999) Brain Res 837:289-297) have also been used as simple, high-resolution histochemical markers of myelin. More recently, fluoromyelin (Kanaan et al. (2005) Am J Physiol Regul Integr Comp Physiol 290:R1105-1114) and NIM (Xiang et al. (2005) J Histochem Cytochem 53:1511-1516) were introduced as novel myelin dyes, which enable quick and selective labeling of myelin in brain tissue sections. Although these myelin-staining techniques are widely used in vitro, none can be applied in vivo due to impermeability of the blood-brain barrier (BBB). The lack of in vivo molecular probes has limited the progress of myelin imaging and hindered efficacy evaluation of novel myelin repair therapies during their development.

SUMMARY OF THE INVENTION

The present invention relates to molecular probes for use in the detection of myelin in a subject. The molecular probes include a compound having the general formula:

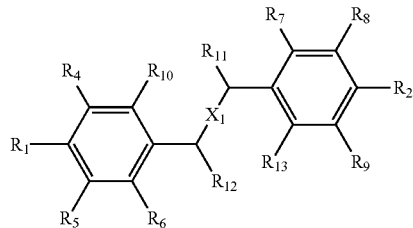

wherein $R_1$ and $R_2$ are each independently a hydrophilic or lipophilic group; wherein $X_1$ is a double or triple bond; each $R_4$-$R_{13}$ is independently selected from the group consisting of H, F, Cl, Br, I, a lower alkyl group, an alkylene group, an alkenyl group, an alkynyl group, an alkoxy group, an aryl group, an aryloxy group, an alkaryl group, an aralkyl group, O, $(CH_2)_n OR'$ (wherein n=1, 2, or 3), $CF_3$, $CH_2$—$CH_2X$, O—$CH_2$—$CH_2X$, $CH_2$—$CH_2$—$CH_2X$, O—$CH_2$—$CH_2X$ (wherein X=F, Cl, Br, or I), CN, C=O, (C=O)—R', $N(R')_2$, $NO_2$, (C=O)N(R')$_2$, O(CO)R', OR', SR', COOR', $R_{ph}$, CR'=CR'—$R_{ph}$, $CR_2'$—$CR_2'$—$R_{ph}$ (wherein $R_{ph}$ represents an unsubstituted or substituted phenyl group, wherein R' is H or a lower alkyl group); wherein $R_{10}$ and $R_{11}$ and/or $R_{12}$ and $R_{13}$ may be linked to form a cyclic ring, wherein the cyclic ring is aromatic, alicyclic, heteroaromatic, or heteroalicyclic; or a pharmaceutically acceptable salt thereof.

In one aspect of the invention, $R_1$ and/or $R_2$ can be selected from the group consisting of H, $NO_2$, $NH_2$, $NHCH_3$, $N(CH_3)_2$, OH, $OCH_3$, $COOCH_3$, SH, $SCH_3$, and alkyl derivatives thereof and each $R_4$-$R_{13}$ is H. The molecular probe in accordance with the present invention can readily enter the brain following systemic or parenteral administration and bind to myelin membranes.

In another aspect of the invention, $R_1$ and $R_2$ are each independently selected from the group consisting of H, $NO_2$, $NH_2$, $NHCH_3$, $N(CH_3)_2$, OH, $OCH_3$, $COOCH_3$, SH, $SCH_3$, and alkyl derivatives thereof, $X_1$ is a double bond, and $R_{10}$ and $R_{11}$ are linked to form a heterocyclic ring.

The present invention also relates to a method of detecting myelin in vivo in an animals's tissue. The method includes administering in vivo to the animal a molecular probe that includes a compound having the general formula:

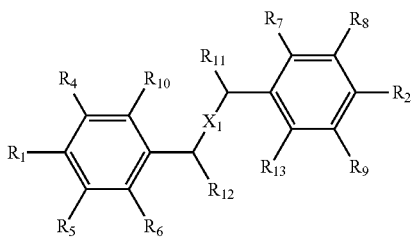

wherein $R_1$ and $R_2$ are each independently a hydrophilic or lipophilic group; wherein $X_1$ is a double or triple bond; each $R_4$-$R_{13}$ is independently selected from the group consisting of H, F, Cl, Br, I, a lower alkyl group, an alkylene group, an alkenyl group, an alkynyl group, an alkoxy group, an aryl group, an aryloxy group, an alkaryl group, an aralkyl group, O, $(CH_2)_nOR'$ (wherein n=1, 2, or 3), $CF_3$, $CH_2$—$CH_2X$, O—$CH_2$—$CH_2X$, $CH_2$—$CH_2$—$CH_2X$, O—$CH_2$—$CH_2X$ (wherein X=F, Cl, Br, or I), CN, C=O, (C=O)—R', $N(R')_2$, $NO_2$, (C=O)$N(R')_2$, O(CO)R', OR', SR', COOR', $R_{ph}$, CR'=CR'—$R_{ph}$, $CR_2'$—$CR_2'$—$R_{ph}$ (wherein $R_{ph}$ represents an unsubstituted or substituted phenyl group, wherein R' is H or a lower alkyl group); wherein $R_{10}$ and $R_{11}$ and/or $R_{12}$ and $R_{13}$ may be linked to form a cyclic ring, wherein the cyclic ring is aromatic, alicyclic, heteroaromatic, or heteroalicyclic; or a pharmaceutically acceptable salt thereof. Following administration of the molecular probe, the animal's tissue is visualized using an in vivo imaging modality.

In one aspect of the invention, $R_1$ and/or $R_2$ can be selected from the group consisting of H, $NO_2$, $NH_2$, $NHCH_3$, $N(CH_3)_2$, OH, $OCH_3$, $COOCH_3$, SH, $SCH_3$, and alkyl derivatives thereof and each $R_4$-$R_{13}$ is H. The molecular probe in accordance with the present invention can readily enter the brain following systemic or parenteral administration and bind to myelin membranes.

In another aspect of the invention, $R_1$ and $R_2$ are each independently selected from the group consisting of H, $NO_2$, $NH_2$, $NHCH_3$, $N(CH_3)_2$, OH, $OCH_3$, $COOCH_3$, SH, $SCH_3$, and alkyl derivatives thereof, $X_1$ is a double bond, and $R_{10}$ and $R_{11}$ are linked to form a heterocylic ring.

The present invention further relates to a method of detecting a myelin related disorder in a subject. The method includes labeling myelin in vivo in the animal's tissue by administering to the animal a molecular probe that includes a compound having the general formula:

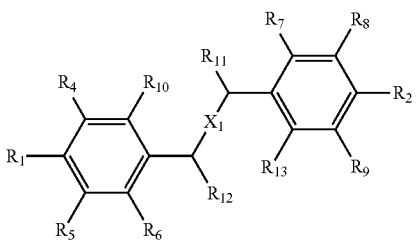

wherein $R_1$ and $R_2$ are each independently a hydrophilic or lipophilic group; wherein $X_1$ is a double or triple bond; each $R_4$-$R_{13}$ is independently selected from the group consisting of H, F, Cl, Br, I, a lower alkyl group, an alkylene group, an alkenyl group, an alkynyl group, an alkoxy group, an aryl group, an aryloxy group, an alkaryl group, an aralkyl group, O, $(CH_2)_nOR'$ (wherein n=1, 2, or 3), $CF_3$, $CH_2$—$CH_2X$, O—$CH_2$—$CH_2X$, $CH_2$—$CH_2$—$CH_2X$, O—$CH_2$—$CH_2X$ (wherein X=F, Cl, Br, or I), CN, C=O, (C=O)—R', $N(R')_2$, $NO_2$, (C=O)$N(R')_2$, O(CO)R', OR', SR', COOR', $R_{ph}$, CR'=CR'—$R_{ph}$, $CR_2'$—$CR_2'$—$R_{ph}$ (wherein $R_{ph}$ represents an unsubstituted or substituted phenyl group, wherein R' is H or a lower alkyl group); wherein $R_{10}$ and $R_{11}$ and/or $R_{12}$ and $R_{13}$ may be linked to form a cyclic ring, wherein the cyclic ring is aromatic, alicyclic, heteroaromatic, or heteroalicyclic; or a pharmaceutically acceptable salt thereof. The distribution of the molecular probe in the animal's tissue is then visualized. The distribution of the molecular probe can then be correlated with a myelin related disorder in the animal.

The present invention further relates to a method of monitoring the efficacy of a remyelination therapy in an animal. The method includes labeling myelin in vivo in the animal's brain tissue with a molecular probe having the general formula:

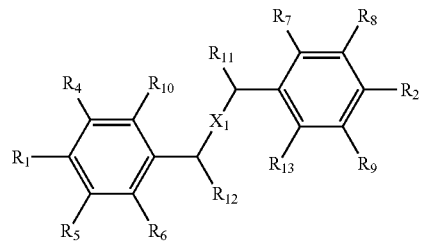

wherein $R_1$ and $R_2$ are each independently a hydrophilic or lipophilic group; wherein $X_1$ is a double or triple bond; each $R_4$-$R_{13}$ is independently selected from the group consisting of H, F, Cl, Br, I, a lower alkyl group, an alkylene group, an alkenyl group, an alkynyl group, an alkoxy group, an aryl group, an aryloxy group, an alkaryl group, an aralkyl group, O, $(CH_2)_nOR'$ (wherein n=1, 2, or 3), $CF_3$, $CH_2$—$CH_2X$, O—$CH_2$—$CH_2X$, $CH_2$—$CH_2$—$CH_2X$, O—$CH_2$—$CH_2X$ (wherein X=F, Cl, Br, or I), CN, C=O, (C=O)—R', $N(R')_2$, $NO_2$, (C=O)$N(R')_2$, O(CO)R', OR', SR', COOR', $R_{ph}$, CR'=CR'—$R_{ph}$, $CR_2'$—$CR_2'$—$R_{ph}$ (wherein $R_{ph}$ represents an unsubstituted or substituted phenyl group, wherein R' is H or a lower alkyl group); wherein $R_{10}$ and $R_{11}$ and/or $R_{12}$ and $R_{13}$ may be linked to form a cyclic ring, wherein the cyclic ring is aromatic, alicyclic, heteroaromatic, or heteroalicyclic; or a pharmaceutically acceptable salt thereof. A distribution of the molecular probe in the animal's tissue is visualized. The distribution of the molecular probe can then be correlated with the efficacy of the remyelination therapy.

The present invention further relates to a method of screening the myelination effects of an agent in an animal. The method includes labeling myelin in vivo in the animal's tissue with a molecular probe having the general formula:

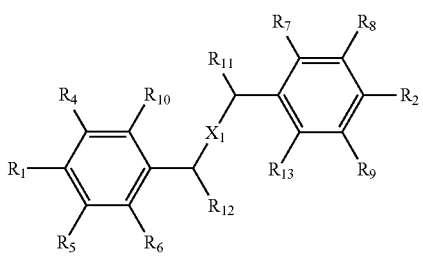

wherein $R_1$ and $R_2$ are each independently a hydrophilic or lipophilic group; wherein $X_1$ is a double or triple bond; each $R_4$-$R_{13}$ is independently selected from the group consisting of H, F, Cl, Br, I, a lower alkyl group, an alkylene group, an alkenyl group, an alkynyl group, an alkoxy group, an aryl group, an aryloxy group, an alkaryl group, an aralkyl group, O, $(CH_2)_n OR'$ (wherein n=1, 2, or 3), $CF_3$, $CH_2$—$CH_2 X$, O—$CH_2$—$CH_2 X$, $CH_2$—$CH_2$—$CH_2 X$, O—$CH_2$—$CH_2 X$ (wherein X=F, Cl, Br, or I), CN, C=O, (C=O)—R', $N(R')_2$, $NO_2$, (C=O)$N(R')_2$, O(CO)R', OR', SR', COOR', $R_{ph}$, CR'=CR'—$R_{ph}$, $CR_2'$—$CR_2'$—$R_{ph}$ (wherein $R_{ph}$ represents an unsubstituted or substituted phenyl group, wherein R' is H or a lower alkyl group); wherein $R_{10}$ and $R_{11}$ and/or $R_{12}$ and $R_{13}$ may be linked to form a cyclic ring, wherein the cyclic ring is aromatic, alicyclic, heteroaromatic, or heteroalicyclic; or a pharmaceutically acceptable salt thereof. A distribution of the molecular probe in the animal's tissue is visualized. The distribution of the molecular probe can then be correlated with the myelination effects of the agent. In one example, the distribution of the molecular probe in the animal's tissue can be compared to a distribution of the molecular probe in a control population to determine the efficacy of the agent.

BRIEF DESCRIPTION OF THE DRAWINGS

The foregoing and other features and advantages of the present invention will become apparent to those skilled in the art to which the present invention relates upon reading the following description with reference to the accompanying drawings, in which:

FIG. 12 illustrates in situ CMC staining of myelin sheaths in the corpus callosum (A:Plp-Akt-DD mouse, B: wild-type mouse); and cerebellum (C:Plp-Akt-DD mouse, D: wild-type mouse).

DETAILED DESCRIPTION

Figure 1:
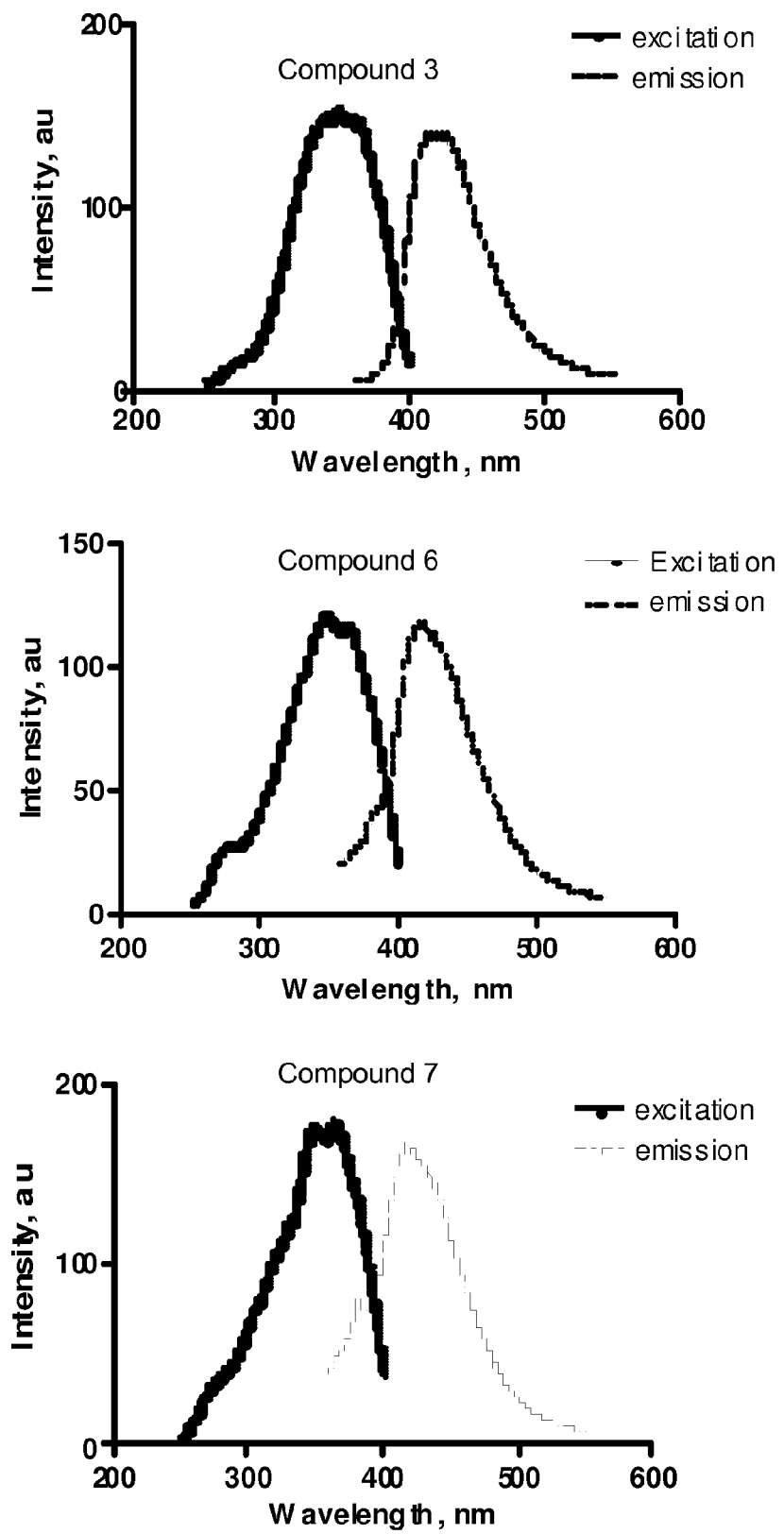
FIG. 1 illustrates excitation and emission spectra of compounds 3, 6 and 7 (1 µM in DMSO). Excitation spectra: emission at 415 nm, 415 nm and 419 nm, range at 250 nm-400 nm, bandwidth at 5 nm, scan at 120 nm/min and integration time of 0.5 sec, maximal excitation wavelength at 347 nm, 350 nm and 363 nm Emission spectra: excitation at 347 nm, 350 nm and 363 nm, range at 360 nm-550 nm, bandwidth at 5 nm, scan at 120 nm/min and integration time of 0.5 sec, maximal emission wavelength at 415 nm, 415 nm and 419 nm.

The present invention relates to molecular probes that upon administration to a mammal (e.g., systemic, parenteral, or intravenous administration) can readily and selectively localize to myelinated regions of the brain, central nervous system, and peripheral nervous system. The molecular probes can bind to myelin membrane and do not bind to a component of degenerating myelin fragments. The molecular probes can also be readily visualized using conventional visualization techniques to indicate myelinated regions of the brain, central nervous system, and peripheral nervous system. The molecular probes can be used in a method of detecting a level of myelination in vivo in a subject, a method of detecting a myelin related disorder in a subject, a method of monitoring the remyelination effects of an agent in an animal, and a method of screening the myelination effects of an agent in an animal.

The molecular probe can include a fluorescent trans-stilbene derivative or a pharmacophore thereof (e.g., coumarin pharmacophore) that is less than about 700 daltons and has a relatively high binding affinity (Kd) (e.g., at least about 1.0 nM) to isolated myelin fractions but a relatively low binding affinity (Kd) to isolated non-myelin fractions.

In an aspect of the invention, the molecular probe can include a fluorescent trans-stilbene derivative having the following formula:

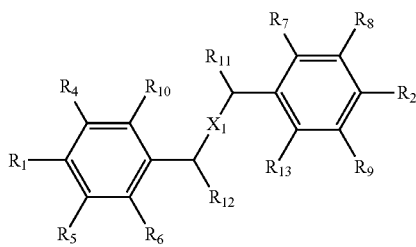

wherein $R_1$ and $R_2$ are each independently a hydrophilic or lipophilic group; wherein $X_1$ is a double or triple bond; each $R_4$-$R_{13}$ is independently selected from the group consisting of H, a halogen group (e.g., F, Cl, Br, I), a lower alkyl group, an alkylene group, an alkenyl group, an alkynyl group, an alkoxy group, an aryl group, an aryloxy group, an alkaryl group, an aralkyl group, O, $(CH_2)_nOR'$ (wherein n=1, 2, or 3), $CF_3$, $CH_2$—$CH_2X$, O—$CH_2$—$CH_2X$, $CH_2$—$CH_2$—$CH_2X$, O—$CH_2$—$CH_2X$ (wherein X=F, Cl, Br, or I), CN, C=O, (C=O)—R', $N(R')_2$, $NO_2$, (C=O)N(R')$_2$, O(CO)R', OR', SR', COOR', $R_{ph}$, CR'=CR'—$R_{ph}$, $CR_2'$, —$CR_2'$—$R_{ph}$ (wherein $R_{ph}$ represents an unsubstituted or substituted phenyl group, wherein R' is H or a lower alkyl group); wherein $R_{10}$ and $R_{11}$ and/or $R_{12}$ and $R_{13}$ may be linked to form a cyclic ring, wherein the cyclic ring is aromatic, alicyclic, heteroaromatic, or heteroalicyclic; or a pharmaceutically acceptable salt thereof.

The phrase "having the formula" or "having the structure" is not intended to be limiting and is used in the same way that the term "comprising" is commonly used.

The term "alkyl" refers to a branched or unbranched saturated hydrocarbon group typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups, such as cyclopentyl, cyclohexyl, and the like. Generally, although again not necessarily, alkyl groups herein contain 1 to about 18 carbon atoms, preferably 1 to about 12 carbon atoms. The term "lower alkyl" intends an alkyl group of 1 to 6 carbon atoms. Substituents identified as "$C_1$-$C_6$ alkyl" or "lower alkyl" can contain 1 to 3 carbon atoms, and more particularly such substituents can contain 1 or 2 carbon atoms (i.e., methyl and ethyl). "Substituted alkyl" refers to alkyl substituted with one or more substituent groups, and the terms "heteroatom-containing alkyl" and "heteroalkyl" refer to alkyl in which at least one carbon atom is replaced with a heteroatom, as described in further detail infra. If not otherwise indicated, the terms "alkyl" and "lower alkyl" include linear, branched, cyclic, unsubstituted, substituted, and/or heteroatom-containing alkyl or lower alkyl, respectively.

The term "alkenyl" refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Generally, although again not necessarily, alkenyl groups can contain 2 to about 18 carbon atoms, and more particularly 2 to 12 carbon atoms. The term "lower alkenyl" refers to an alkenyl group of 2 to 6 carbon atoms, and the specific term "cycloalkenyl" intends a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" refers to a linear or branched hydrocarbon group of 2 to 24 carbon atoms containing at least one triple bond, such as ethynyl, n-propynyl, and the like. Generally, although again not necessarily, alkynyl groups can contain 2 to about 18 carbon atoms, and more particularly can contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" refers to an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Preferred substituents identified as "$C_1$-$C_6$ alkoxy" or "lower alkoxy" herein contain 1 to 3 carbon atoms, and particularly preferred such substituents contain 1 or 2 carbon atoms (i.e., methoxy and ethoxy).

The term "aryl" refers to an aromatic substituent containing a single aromatic ring or multiple aromatic rings that are fused together, directly linked, or indirectly linked (such that the different aromatic rings are bound to a common group such as a methylene or ethylene moiety). Aryl groups can contain 5 to 20 carbon atoms, and particularly preferred aryl groups can contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituent, in which at least one carbon atom is replaced with a heteroatom, as will be described in further detail infra. If not otherwise indicated, the term "aryl" includes unsubstituted, substituted, and/or heteroatom-containing aromatic substituents.

The term "aryloxy" as used herein refers to an aryl group bound through a single, terminal ether linkage, wherein "aryl" is as defined above. An "aryloxy" group may be represented as —O-aryl where aryl is as defined above. Preferred aryloxy groups contain 5 to 20 carbon atoms, and particularly preferred aryloxy groups contain 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. Exemplary aralkyl groups contain 6 to 24 carbon atoms, and particularly preferred aralkyl groups contain 6 to 16 carbon atoms. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. Alkaryl groups include, for example, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like.

The term "cyclic" refers to alicyclic or aromatic substituents that may or may not be substituted and/or heteroatom containing, and that may be monocyclic, bicyclic, or polycyclic.

The terms "halo" and "halogen" are used in the conventional sense to refer to a chloro, bromo, fluoro or iodo substituent.

The term "heteroatom-containing" as in a "heteroatom-containing alkyl group" (also termed a "heteroalkyl" group) or a "heteroatom-containing aryl group" (also termed a "heteroaryl" group) refers to a molecule, linkage or substituent in which one or more carbon atoms are replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc.

By "substituted" as in "substituted alkyl," "substituted aryl," and the like, as alluded to in some of the aforementioned definitions, is meant that in the alkyl, aryl, or other moiety, at least one hydrogen atom bound to a carbon (or other) atom is replaced with one or more non-hydrogen substituents. In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl, alkenyl, and aryl" is to be interpreted as "substituted alkyl, substituted alkenyl, and substituted aryl." Analogously, when the term "heteroatom-containing" appears prior to a list of possible heteroatom-containing groups, it is intended that the term apply to every member of that group. For example, the phrase "heteroatom-containing alkyl, alkenyl, and aryl" is to be interpreted as "heteroatom-containing alkyl, substituted alkenyl, and substituted aryl."

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

In one aspect of the invention, $R_1$ and/or $R_2$ can be selected from the group consisting of H, $NO_2$, $NH_2$, $NHCH_3$, $N(CH_3)_2$, OH, $OCH_3$, $COOCH_3$, SH, $SCH_3$, and alkyl derivatives thereof and each $R_4$-$R_{13}$ is H.

In one example of the invention, the molecular probe can include a fluorescent stilbene derivative having the following formula:

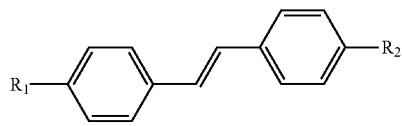

wherein $R_1$ and $R_2$ are each independently selected from the group consisting of H, $NO_2$, $NH_2$, $NHCH_3$, $N(CH_3)_2$, OH, $OCH_3$, $COOCH_3$, SH, $SCH_3$, and alkyl derivatives thereof or a pharmaceutically acceptable salt thereof.

In a further aspect the, the molecular probe can be selected from the following general structures:

Compound 3

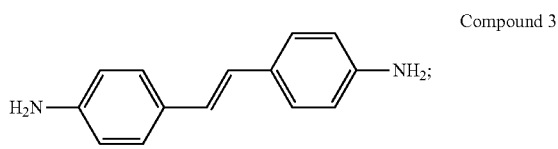

Compound 6

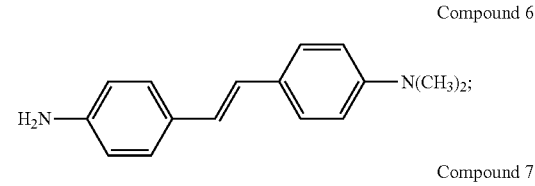

Compound 7

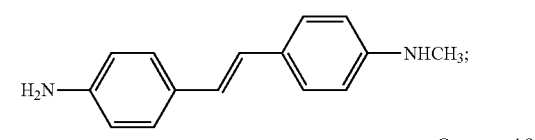

Compound 9

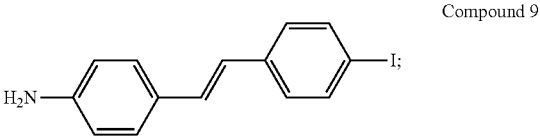

or pharmaceutically acceptable salts thereof.

In another aspect of the invention, the molecular probe can include a fluorescent coumarin derivative that is a pharmacophore of trans-stilbene. In an aspect of the invention, $R_1$ and $R_2$ are each independently selected from the group consisting of H, $NO_2$, $NH_2$, $NHCH_3$, $N(CH_3)_2$, OH, $OCH_3$, $COOCH_3$, SH, $SCH_3$, and alkyl derivatives thereof, $X_1$ is a double bond, and $R_{10}$ and $R_{11}$ are linked to form a heterocylic ring.

In one example, the fluorescent coumarin derivative can a pharmacophore of trans-stilbene having the following formula:

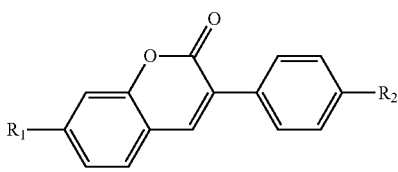

wherein $R_1$ and $R_2$ are each independently selected from the group consisting of H, $NO_2$, $NH_2$, $NHCH_3$, $N(CH_3)_2$, OH, $OCH_3$, $COOCH_3$, SH, $SCH_3$, and alkyl derivatives thereof; and pharmaceutically acceptable salts thereof.

In another example, the fluorescent coumarin derivative can be a pharmacophore of trans-stilbene having the following formula:

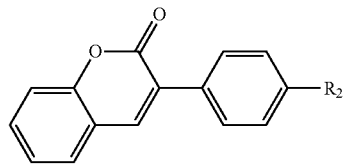

wherein $R_1$ and $R_2$ are each independently selected from the group consisting of H, $NO_2$, $NH_2$, $NHCH_3$, $N(CH_3)_2$, OH, $OCH_3$, $COOCH_3$, SH, $SCH_3$, and alkyl derivatives thereof; and pharmaceutically salts thereof.

In a further example, the fluorescent coumarin derivative can be a pharmacophore of stilbene having the following formula:

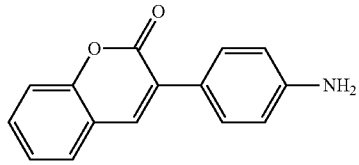 [SMILES: Nc1ccc(-c2cc3ccccc3oc2=O)cc1]

or a pharmaceutically acceptable salt thereof.

The foregoing formulae represent the general structures of fluorescent trans-stilbene compounds found to be effective molecular probes for labeling myelin in vivo as well as in vitro as described in the examples below. They are characterized by their ability to be administered to a mammal or subject parenterally and selectively localize to myelinated regions in the brain, central nervous system, and peripheral nervous system via direct binding to myelin membranes and not bind to degenerating myelin fragments. The molecular probes are unique in that they exhibit negligible toxicities as demonstrated in both preclinical and clinical settings, making them suitable candidates for clinical imaging modalities and translational studies. For example, once radiolabelled with positron-emitting radionuclide, they can be used for positron emission tomography to detect and quantify myelin contents in vivo.

When referring to the terms "fluorescent trans-stilbene" or "fluorescent trans-stilbene derivative" or "fluorescent trans-stilbene compound" in the specification and the claims, it is intended that the terms encompass not only the specified molecular entity but also its pharmaceutically acceptable, pharmacologically active analogs, including, but not limited to, salts, esters, amides, prodrugs, conjugates, active metabolites, and other such derivatives, analogs, and related compounds.

By "pharmaceutically acceptable" is meant a material that is not biologically or otherwise undesirable, i.e., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug administration. "Pharmacologically active" (or simply "active") as in a "pharmacologically active" derivative or analog, refers to a derivative or analog having the same type of pharmacological activity as the parent compound and approximately equivalent in degree.

As used herein, the term "pharmaceutically acceptable salts" or complexes refers to salts or complexes that retain the desired biological activity of the parent compound and exhibit minimal, if any, undesired toxicological effects. Nonlimiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, palmoic acid, alginic acid, polyglutamic acid, naphthalenesulfonic acids, naphthalenedisulfonic acids, and polygalacturonic acid; (b) base addition salts formed with cations such as sodium, potassium, zinc, calcium, bismuth, barium, magnesium, aluminum, copper, cobalt, nickel, cadmium, sodium, potassium, and the like, or with an organic cation formed from N,N-dibenzylethylene-diamine, ammonium, or ethylenediamine; or (c) combinations of (a) and (b); e.g., a zinc tannate salt or the like.

Typically, the molecular probe can be formulated into solution prior to use. In one example, a molecular probe solution includes a 10 mM molecular probe solution. A molecular probe solution can also contain saline, DMSO, and HCL. One skilled in the art can utilize the molecular probe with pharmaceutical carriers and/or excipients in varying concentrations and formulations depending on the desired use.

In some embodiments of the present invention, the molecular probe can be radiolabeled to aid in the detection of the molecular probe once it binds to myelin. A 'radiolabel' as used herein is any compound that has been joined with a radioactive substance. Examples of radiolabels include positron emitting $^3H$, $^{125}I$, $^{11}C$, and $^{18}F$ radiolabels.

In an embodiment of the invention, the molecular probe can be coupled to a chelating group (with or without a chelated metal group) to improve the MRI contrast properties of the molecular probe. In one example, as disclosed in U.S. Pat. No. 7,351,401 which is herein incorporated by reference in its entirety, the chelating group can be of the form W-L or V—W-L, wherein V is selected from the group consisting of —COO—, —CO—, —$CH_2O$— and —$CH_2NH$—; W is —$(CH_2)n$ where n=0, 1, 2, 3, 4, or 5; and L is:

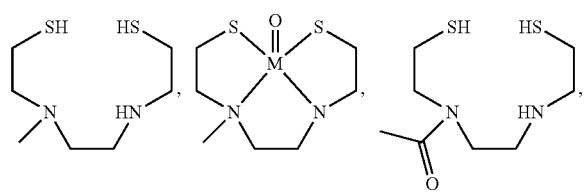

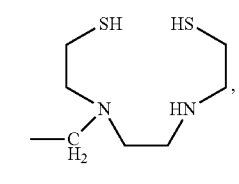

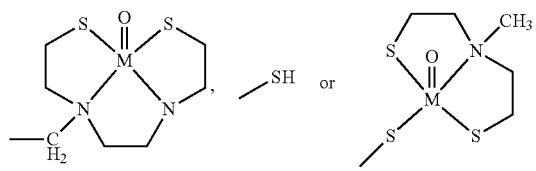

wherein M is selected from the group consisting of Tc and Re; or

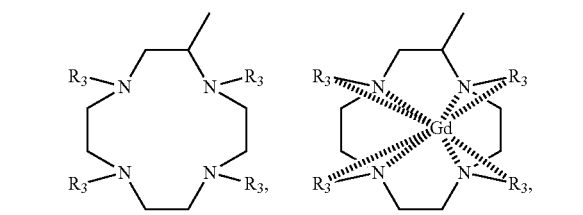

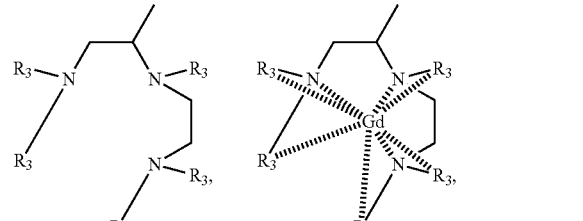

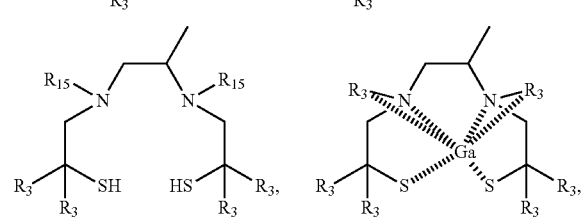

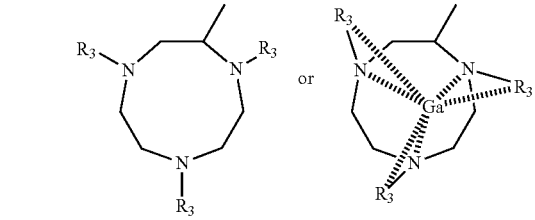

wherein each $R_3$ is independently is selected from one of:

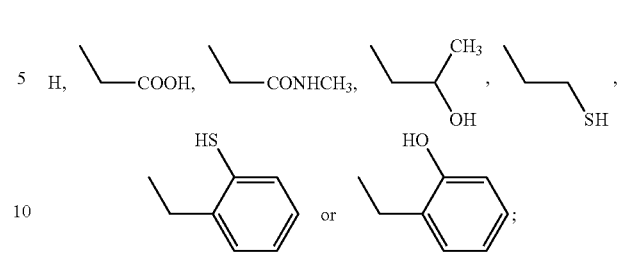

or a myelin binding, chelating compound (with or without a chelated metal group) or a water soluble, non-toxic salt thereof of the form:

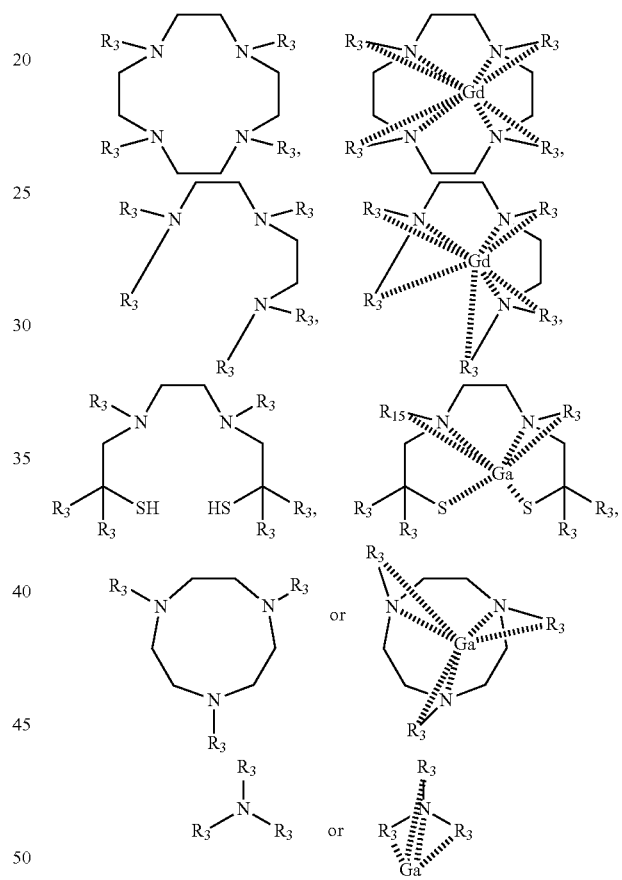

wherein each $R_3$ independently is selected from one of:

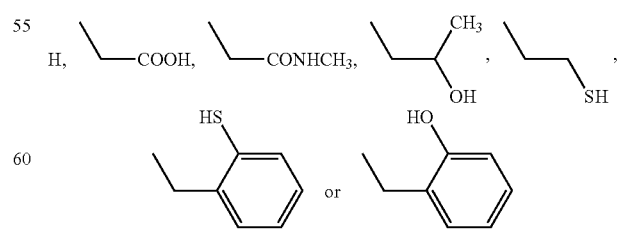

The chelating group can be coupled to at least one terminal benzene groups or the $R_1$ or $R_2$ groups. In one example, the chelating group can be coupled to terminal amino $R_1$ and/or $R_2$ group through a carbon chain link. The carbon chain link can comprise, for example about 2 to about 10 methylene groups and have a formula of, for example, $(CH_2)_n$, wherein n=2 to 10.

In one example, the molecular probe with the chelating group can have the following formula:

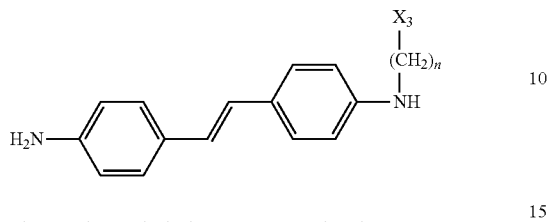

wherein $X_3$ is a chelating group and n is 2 to 10; or a pharmaceutically acceptable salt thereof.

In another example, the molecular probe with the chelating group can have the following formula:

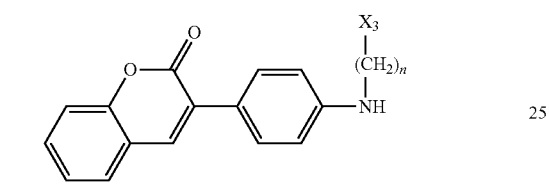

wherein $X_3$ is a chelating group and n is 2 to 10; or a pharmaceutically acceptable salt thereof.

In another example, the molecular probe with the chelating group can have the following formula:

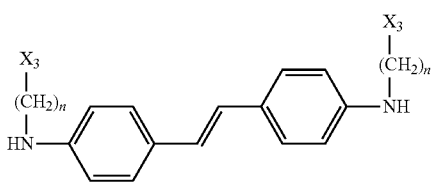

wherein $X_3$ is a chelating group and n is 2 to 10; or a pharmaceutically acceptable salt thereof.

In another embodiment, the molecular probe can be coupled to a near infrared group to improve the near infrared imaging of the molecular probe. Examples of near infrared imaging groups that can be coupled to the molecular probe include:

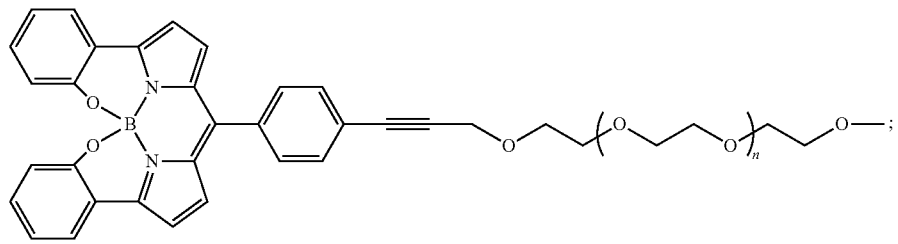

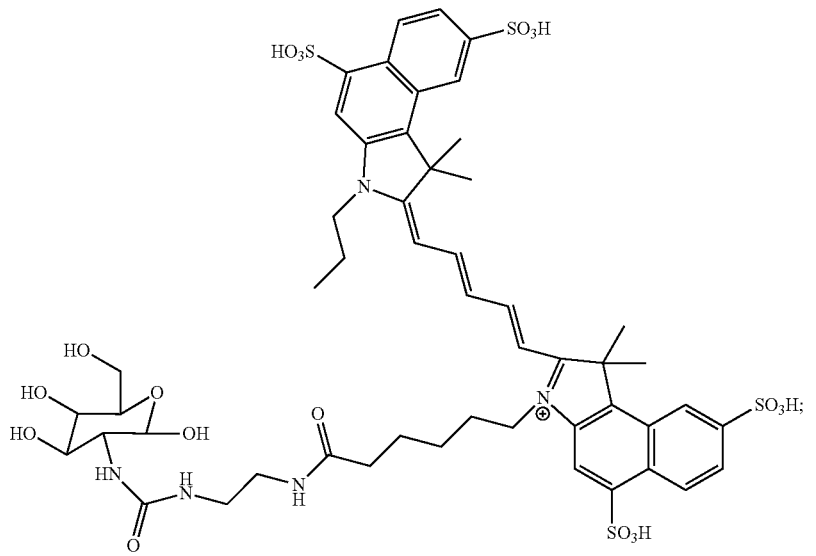

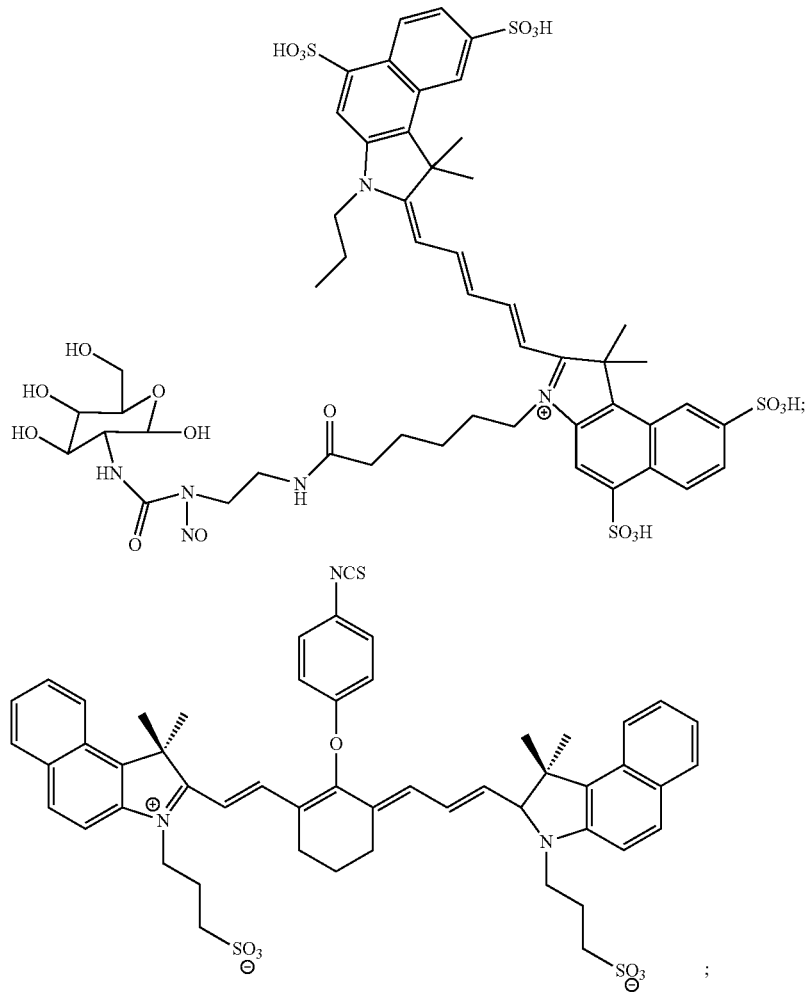
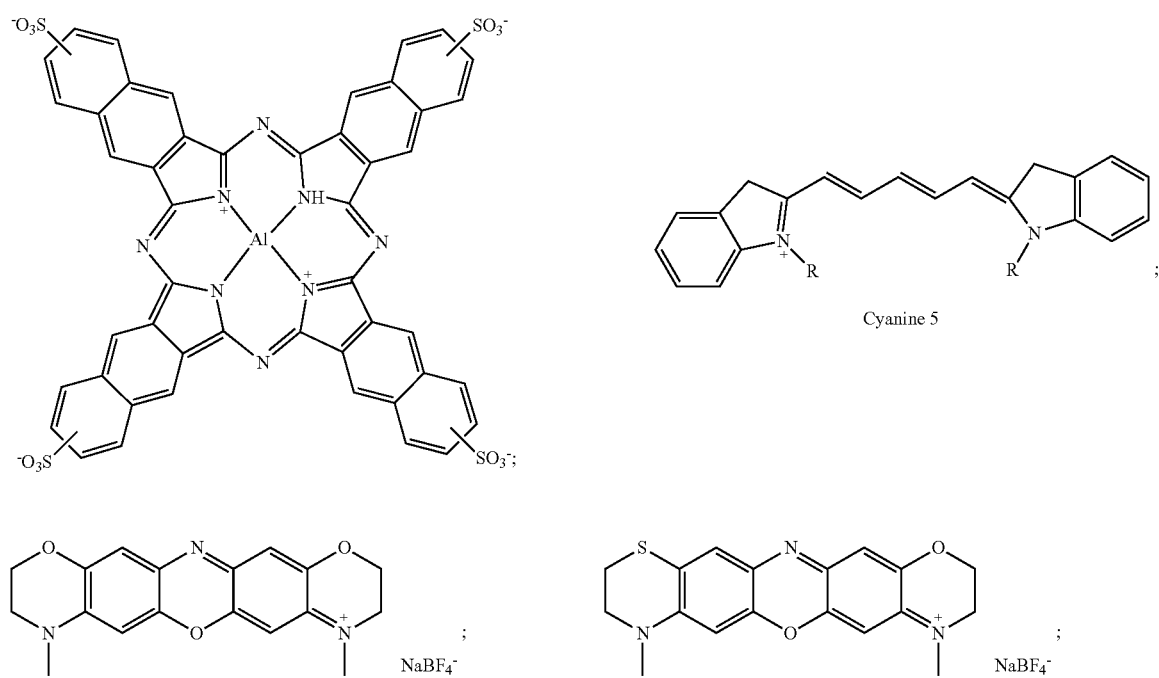

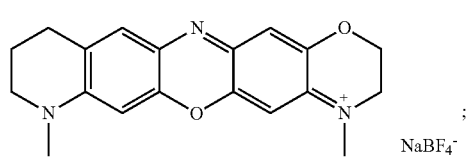
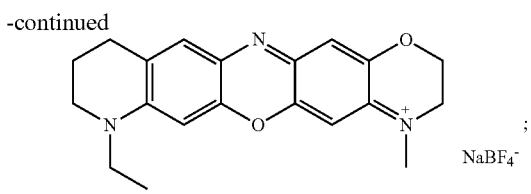

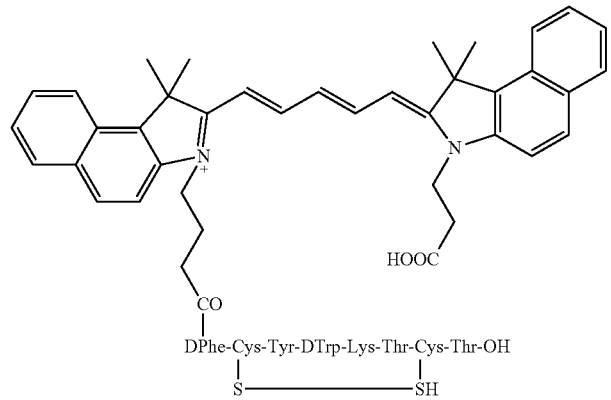
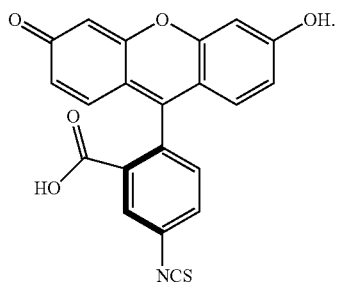

These near infrared imaging groups are disclosed in, for example, Tetrahedron Letters 49(2008) 3395-3399; Angew. Chem. Int. Ed. 2007, 46, 8998-9001; Anal. Chem. 2000, 72, 5907; Nature Biotechnology vol 23, 577-583; Eur Radiol (2003) 13: 195-208; and Cancer 67: 1991 2529-2537, which are herein incorporated by reference in their entirety.

The near infrared imaging group can be coupled to at least one terminal benzene groups, or the $R_1$ or $R_2$ groups. In one example, the near infrared imaging group can be coupled to at least one terminal benzene group.

In one example, the molecular probe with the near infrared imaging group can have the following formula:

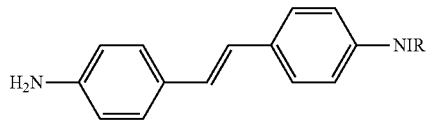

wherein NIR is a near infrared imaging group; or a pharmaceutical salt thereof.

In another example, the molecular probe with the near infrared imaging group can have the following formula:

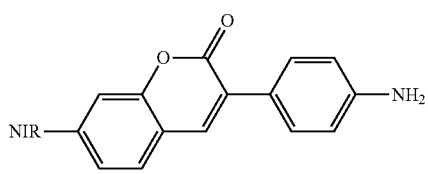

wherein NIR is a near infrared imaging group; or a pharmaceutical salt thereof.

By way of example, the molecular probe can include a compound having the following formula:

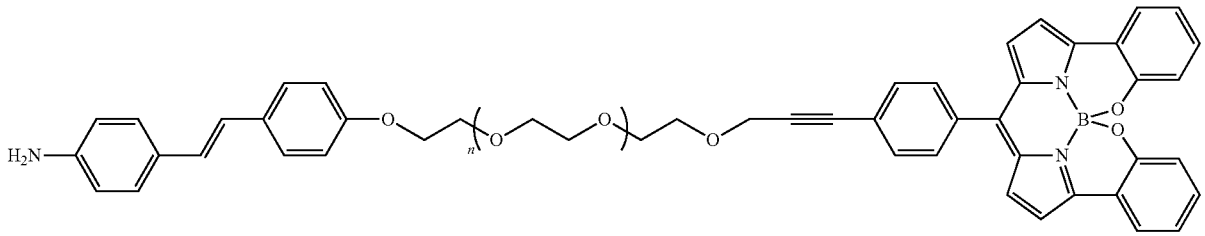

wherein n is 3 to 10; or a salt thereof.

In certain embodiments of the present invention, the molecular probes described herein can be contacted with an animal's brain tissue central nervous system, and/or peripheral nervous system and utilized for labeling and detecting myelinated regions of an animal's brain tissue, central nervous system, and/or peripheral nervous system. Myelinated regions of an animal's brain are typically found in the white matter of the brain in the myelin sheaths of neuronal axons. Myelin is an outgrowth of glial cells, more specifically oligodendrocytes, which serve as an electrically insulating phospholipid layer surrounding axons of many neurons. For purposes of the present invention, an animal's brain tissue is typically a mammal's brain tissue, such as a primate, e.g., chimpanzee or human; cow; dog; cat; a rodent, e.g., guinea pig, rat, mouse; rabbit; or a bird; reptile; or fish.

In some embodiments, the molecular probes described herein can be used for the in vivo detection and localization of myelinated regions of an animal's brain, central nervous system, and/or peripheral nervous system. The molecular probe can be administered to the animal as per the examples contained herein, but typically through intravenous injection. "Administered", as used herein, means provision or delivery molecular probes in an amount(s) and for a period of time(s) effective to label myelin in an animal's brain central nervous system, and/or peripheral nervous system. The molecular probes can be administered to the animal can be enterally or parenterally in a solid or liquid. Enteral route includes oral, rectal, topical, buccal, and vaginal administration. Parenteral route includes intravenous, intramuscular, intraperitoneal, intrasternal, and subcutaneous injection or infusion.

An example of a dosing regimen is to administer about 40- about 50 mg/kg by weight to the animal. In one example at 5 min, the brain concentration of probe can range between about 4% to 24% ID/g to ensure sufficient visualization of the myelinated regions of the brain, central nervous system, and/or peripheral nervous system.

The molecular probes of the present invention can be used for neuroanatomical or neuropathological studies. Researchers studying normal brains can employ this method to examine the morphology and distribution of myelinated tissue in an animal. "Distribution" as used herein is the spatial property of being scattered about over an area or volume. In this case the "distribution of myelinated tissue" is the spatial property of myelin being scattered about over an area or volume included in the animal's brain, central nervous system, or peripheral nervous system tissue. Researchers interested in neurotoxicology and neuropathology can also use this method in several ways. One way is to infer demyelination by the absence of the molecular probe labeling compared to normal control tissue (e.g., normal brain). A second way is to study morphological changes in the myelin such as a fragmented or beaded appearance of the myelin sheath. In yet another embodiment of the present invention, one skilled in the art can assess and quantify changes in myelin content in vivo.

In other aspects of the present invention, myelin in an animal's brain, central nervous system, and/or peripheral nervous system can be visualized and quantified using an in vivo imaging modality. The molecular probe may be visualized any time post administration depending on the application as typical molecular probes embodied in the present invention have a low clearance rate due to specific binding in the myelinated regions (e.g. at 60 min, the brain concentration of probe can be ≤50% of 5 min value to ensure that half time retention in normally myelinated brain is 60 min or longer).

An in vivo imaging modality as used herein is an imaging modality capable of visualizing molecular probes described herein in vivo (within a living organism). An example of an in vivo imaging modality is positron emission tomography (PET). PET is a functional imaging technique that can detect chemical and metabolic change at the molecular level. To function as a PET imaging molecular probe, embodiments of the present invention must meet a set of biological requirements known to the skilled artisan, some of which may include lipophilicity, binding affinity, binding specificity, brain uptake, retention, and metabolism. Another example of an in vivo imaging modality is MicroPET. MicroPET is a high resolution positron emission tomography scanner designed for imaging small laboratory animals. Other examples of imaging modalities that can be used in accordance with the present invention include magnetic resonance imaging (MRI), near infrared (NIR) imaging, fluorescent microscopy, and mutiphoton microscopy.

For directly monitoring myelin changes in the white matter of a subject, embodiments of the invention can readily penetrate the blood-brain barrier (BBB) and directly bind to the myelinated white matter in proportion to the extent of myelination. Radiolabeled molecular probes of the present invention can be used in conjunction with PET as imaging markers to directly assess the extent of total lesion volumes associated with demyelination. This can provide a direct clinical efficacy endpoint measure of myelin changes and identify effective therapies aimed at protection and repair of axonal damages.

The molecular probes of the present invention can also be used to diagnose a myelination related disorder in an animal through the use of in vivo myelin labeling. Thus, in certain embodiments of the present invention, solutions containing the molecular probes describe herein can be used in the detection of myelin related disorders in an animal.

Methods of detecting a myelin related disorder include the steps of labeling myelin in vivo in the animal's brain tissue with a molecular probe described herein, visualizing a distribution of the molecular probe in the animal's brain tissue as described above and in the examples, and then correlating the distribution of the molecular probe with a myelin related disorder in the animal. In one example of detecting a myelin related disorder, the methods described herein can be used to compare myelinated axonal regions of the brain in the normal tissues of control populations to those of a suspect animal. If the suspect animal has a myelin related disorder, myelin may be virtually absent in lesioned areas thus indicating the presence of a myelin related disorder.

Myelination disorders can include any disease, condition (e.g., those occurring from traumatic spinal cord injury and cerebral infarction), or disorder related to demylination, remylination, or dysmyelination in a subject. A myelin related disorder as used herein can arise from a myelination related disorder or demyelination resulting from a variety of neurotoxic insults. Demyelination is the act of demyelinating, or the loss of the myelin sheath insulating the nerves, and is the hallmark of some neurodegenerative autoimmune diseases, including multiple sclerosis, transverse myelitis, chronic inflammatory demyelinating polyneuropathy, and Guillain-Bane Syndrome. Leukodystrophies are caused by inherited enzyme deficiencies, which cause abnormal formation, destruction, and/or abnormal turnover of myelin sheaths within the CNS white matter. Both acquired and inherited myelin disorders share a poor prognosis leading to major disability. Thus, some embodiments of the present invention can include methods for the detection of neurodegenerative autoimmune diseases in an animal and more specifically the detection of multiple sclerosis in an animal.

Another embodiment of the present invention includes a method of monitoring the efficacy of a remyelination therapy in an animal. Remyelination is the repair of damaged or replacement of absent myelin in an animal's brain tissue. The methods described include the steps of labeling myelin in vivo in the animal's brain tissue with a molecular probe described herein, then visualizing a distribution of the molecular probe in the animal's brain tissue (e.g. with a in vivo imaging modality as described herein), and then correlating the distribution of the molecular probe as visualized in the animal's brain with the efficacy of the remyelination therapy. It is contemplated that the labeling step can occur before, during, and after the course of a therapeutic regimen in order to determine the efficacy of the therapeutic regimen. One way to assess the efficacy of a remyelination therapy is to compare the distribution of the molecular probe before remyelination therapy with the distribution of the molecular probe after remyelination therapy has commenced or concluded.

Remyelination therapy as used herein refers to any therapy leading to a reduction in severity and/or frequency of symptoms, elimination of symptoms and/or underlying cause, prevention of the occurrence of symptoms and/or their underlying cause, and improvement or remediation of damage related to demyelination. For example, a remyelination therapy can include administration of a therapeutic agent, therapies for the promotion of endogenous myelin repair, or a cell based therapy (e.g., a stem-cell based therapy).

In another embodiment of the present invention, methods are provided for screening for a myelination response in an animal's brain tissue to an agent. The method includes the initial step of administering an agent to the animal. Myelin in the animal's brain tissue is labeled in vivo with a molecular probe in accordance with the present invention. A distribution of the molecular probe in the animal's brain tissue is then visualized using a conventional visualization modality. Finally, the distribution of the molecular probe with the myelination response in the animal's brain tissue is correlated to the agent. One way to assess the myelination response in the animal's brain tissue is to compare the distribution of the molecular probe in an animal's brain tissue, which has been treated with a suspect agent with the distribution of the molecular probe in the brain tissue of a control population. "Control Population" as used herein is defined as a population or a tissue sample not exposed to the agent under study but otherwise as close in all characteristics to the exposed group as possible.

The molecular probes described herein can be used to determine if an agent of interest has the potential to modulate demyelination, remyelination, or dysmyelination of axonal regions of an experimental animal's brain tissue.

Example 1

We have identified a series of stilbene derivatives that displayed promising in vitro and in situ properties for imaging of myelinated white matter. Compared to previously reported myelin-imaging probes, these compounds showed improved solubility and binding affinity. The synthesis and biological evaluation of trans-stilbene derivatives is described below.

Chemical Synthesis

Synthesis of stilbene derivatives was achieved through Horner-Wittig reaction as shown below.

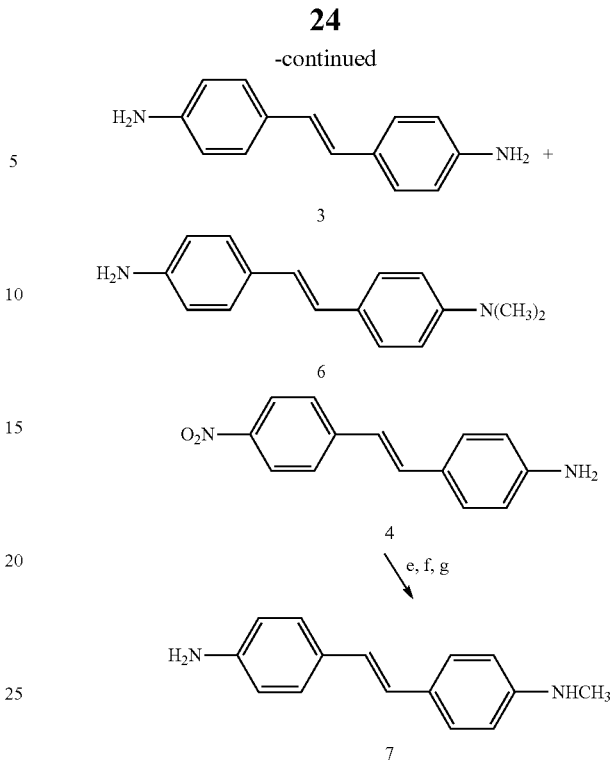

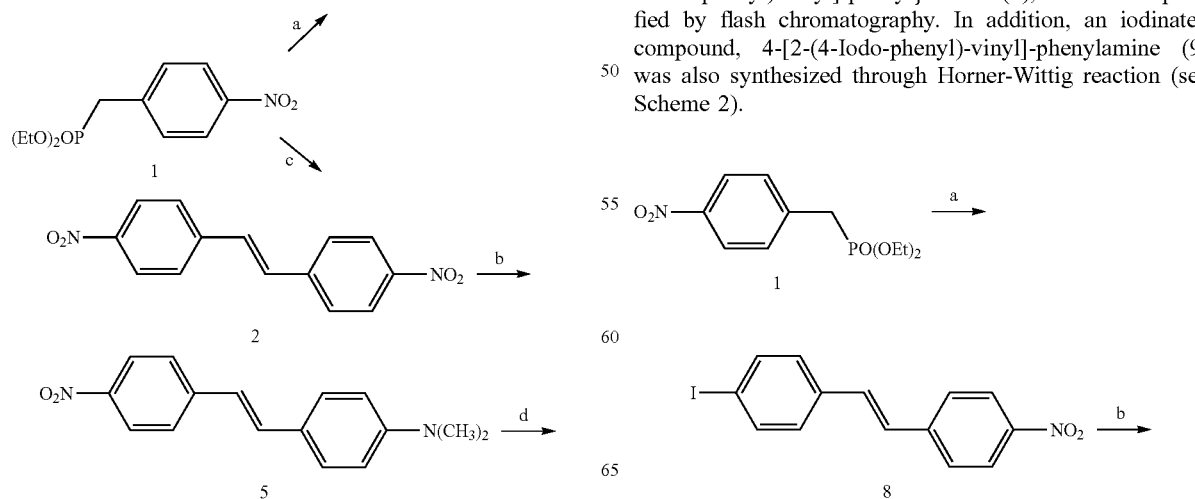

In this study, 4-nitrobenzaldehyde and 4-dimethylaminobenzaldehyde were employed to react with a Horner-Wadsworth-Emmons reagent, (p-nitrobenzyl)-phosphonic acid diethyl ester (1), to yield (E)-4,4'-dinitro-stilbene (2) and (E)-dimethyl-{4-[2-(4-nitro-phenyl)-vinyl]-phenyl}-amine (5). Further reduction of the nitro groups of 2 and 5 in the presence of $SnCl_2$ in ethanol, furnished (E)-4,4'-diamino-trans-stilbene (3) and (E)-dimethyl-{4-[2-(4-amino-phenyl)-vinyl]-phenyl}-amine (6). Reduction of 2 also yielded a less polar, semi-reduced compound, 4-[2-(4-nitro-phenyl)-vinyl]-phenylamine (4) that was successfully separated and characterized by HNMR and HR-MS. Compound 4 was further protected with trifluoroacetic anhydride. Subsequently, methylation with iodomethane in the presence of potassium carbonate followed by hydrolysis and reduction yielded the monoalkylated compound, N-methyl-{4-[2-(4-amino-phenyl)-vinyl]-phenyl}-amine (7), which was purified by flash chromatography. In addition, an iodinated compound, 4-[2-(4-Iodo-phenyl)-vinyl]-phenylamine (9) was also synthesized through Horner-Wittig reaction (see Scheme 2).

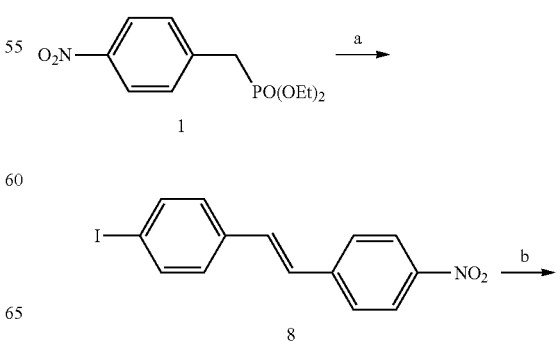

-continued

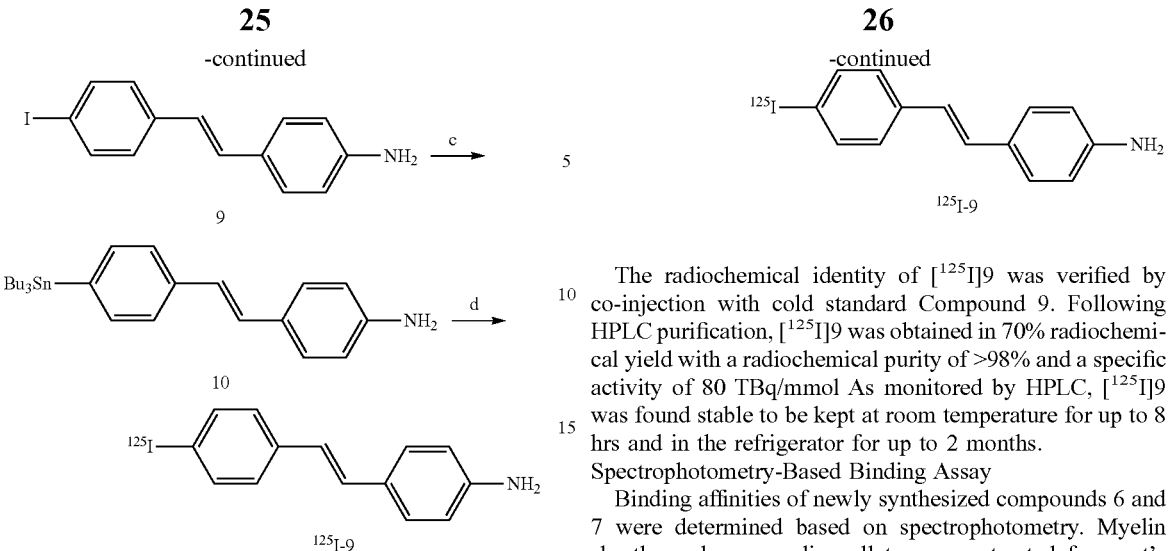

4-Iodo-benzaldehyde readily reacted with 1 in DMF in the presence of NaH. Subsequent reduction with SnCl$_2$ yielded Compound 9. Compounds 3, 6 and 7 are fluorescent compounds and soluble in EtOH, CH$_2$Cl$_2$, DMSO and other organic solvents. The excitation and emission spectra of 3, 6 and 7 (1 μM in DMSO), as recorded using a Cary Eclipse Fluorescent Spectrophotometer, are shown in FIG. 1. The maximal excitation wavelengths were found at 347 nm, 350 nm and 363 nm, and the maximal emission wavelengths were determined at 415 nm, 415 nm and 419 nm for 3, 6, and 7, respectively.

Compound 9 was selected for radiolabelling with $^{125}$I. The radiolabeling precursor, 4-[2-(4-tributylstannanyl-phenyl)-vinyl]-phenylamine (10), was first synthesized directly from the cold standard compound 9, in which the iodo group was replaced with a tributyltin group in the presence of Pd(PPh$_3$)$_4$. Iododestannylation reaction using no-carrier-added sodium [$^{125}$I] iodide in the presence of hydrogen peroxide as the oxidant yielded [$^{125}$I]9 (Scheme 2).

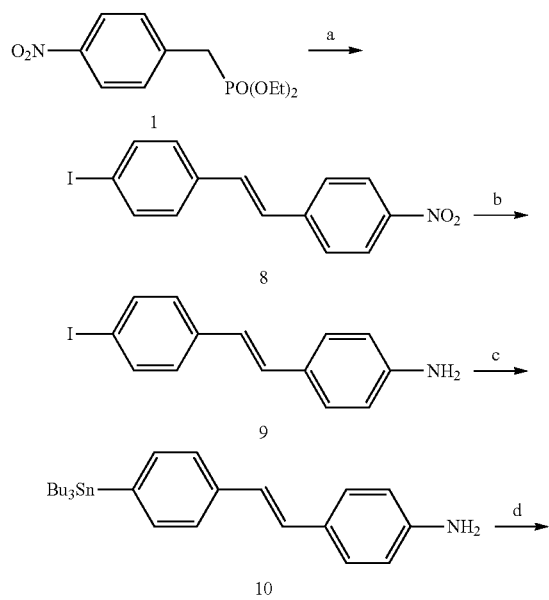

The radiochemical identity of [$^{125}$I]9 was verified by co-injection with cold standard Compound 9. Following HPLC purification, [$^{125}$I]9 was obtained in 70% radiochemical yield with a radiochemical purity of >98% and a specific activity of 80 TBq/mmol As monitored by HPLC, [$^{125}$I]9 was found stable to be kept at room temperature for up to 8 hrs and in the refrigerator for up to 2 months.

Spectrophotometry-Based Binding Assay

Binding affinities of newly synthesized compounds 6 and 7 were determined based on spectrophotometry. Myelin sheaths and non-myelin pellets were extracted from rat's brain homogenates according to subcellular fraction protocol (Martenson, R. E.; Deibler, G. E.; Kies, M. W. Extraction of rat myelin basic protein free of other basic proteins of whole central nervous system tissue. An analysis of its electrophoretic heterogeneity. *J Biol Chem* 1969, 244, 4268-4272). Briefly, the homogenates were successively mixed with different concentrations of sucrose and spun in a Beckman ultracentrifuge. Myelin sheaths and non-myelin containing pellets were well separated according to their different densities and located in different layers of sucrose. The proteins were then collected and washed thoroughly with Colman buffer (10 mM). The desired proteins were aliquoted and frozen at −80° C. for up to 6 months without noticeable change in its properties determined by electrophoresis (data not shown). Prior to binding assays, the protein fractions (myelin and pellet) were thawed and diluted with PBS (10 mM, pH 7.0). A series of concentrations of the protein fractions were incubated with tested compounds (6 and 7, 12.5 μM) for 1 h at room temperature. The free and bound tested compounds were then separated by centrifuging at 6000 rpm for 10 min and quantified.

Figure 2:
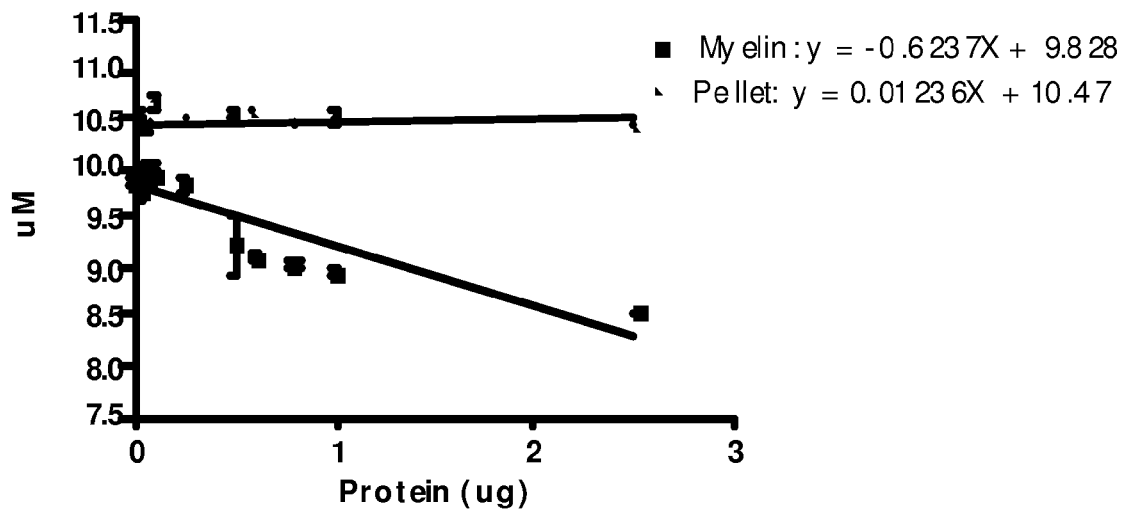
FIG. 2 illustrates plots of the concentrations of free, unbound 6 and 7 following incubation with isolated myelin fractions and non-myelin pellets based upon a spectroscopic assay. In these assays, 10 µM of 6 and 7 was added to each solution containing myelin fractions or non-myelin pellets at various concentrations ranging from 0-2.5 µg per tube. Each data point was repeated in triplicate and an average was used.
Figure 2:
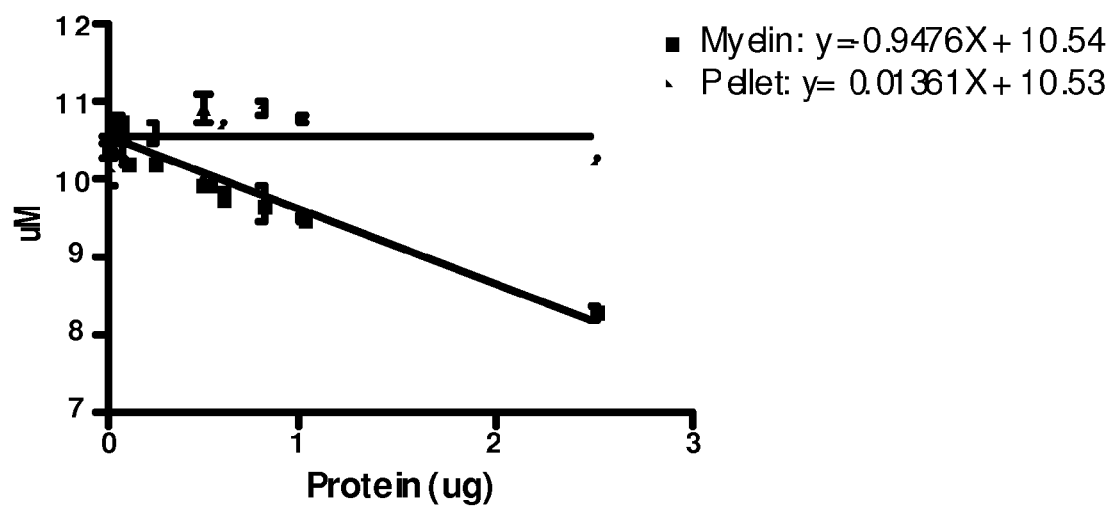

As shown in FIG. 2, when incubated with non-myelin pellet, the concentrations of free, unbound 6 and 7 were not reduced despite the increased concentration of non-myelin pellet. The concentrations of free 6 and 7 remained constant and close to the total concentration (10.47 μM for 6 and 10.53 μM for 7) initially used, suggesting there was no binding to the non-myelin fractions. In contrast, when incubated with myelin fractions, the concentrations of unbound 6 and 7 decreased proportionally when the concentrations of myelin fractions were increased, suggesting that specific binding interactions exist between the test compounds and the myelin fractions.

Radioligand-Based Binding Assays

Figure 3:
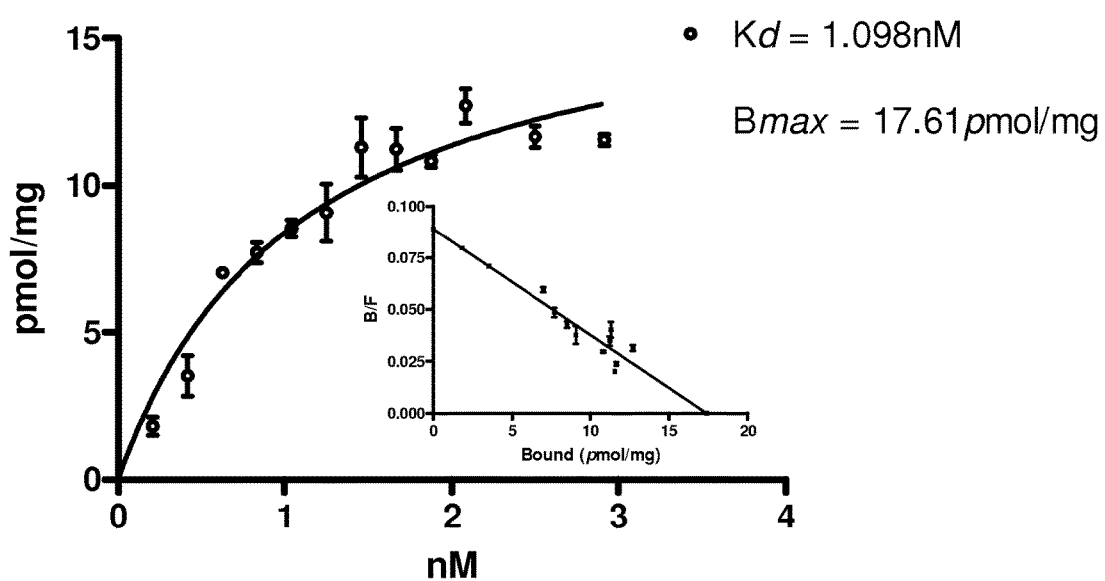
FIG. 3 illustrates saturation and scatchard plots of [$^3$H] BMB binding to isolated myelin fractions. [$^3$H]BMB displayed one-site binding. High-affinity binding with dissociation constant (Kd) values in a nanomolar range was obtained (Kd)) 1.098 nM.
Figure 4:
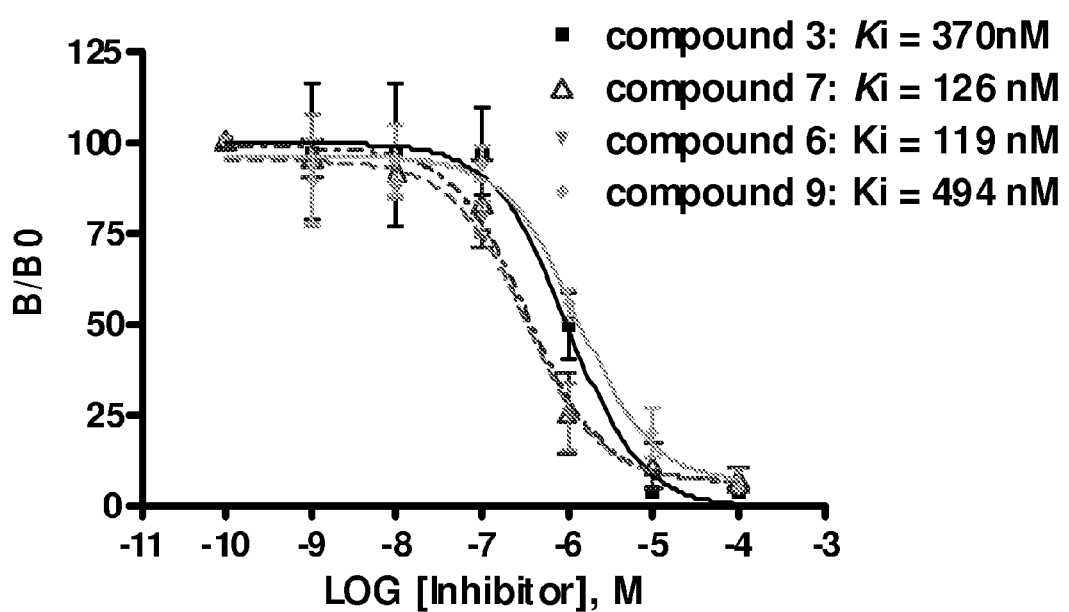
FIG. 4 illustrates plots of competition binding assays of test compounds using [$^3$H]BMB as the radioligand in isolated myelin fractions. The concentrations that inhibited 50% of specific binding of [$^3$H]BMB ($IC_{50}$ values) were converted to inhibition constant (Ki). Ki values were calculated using the Cheng-Prusoff equation: Ki=$IC_{50}$/(1+[L]/Kd), where [L] is the concentration of [$^3$H]BMB used in the assay. Data are means of three independent measurements done in duplicate.

In vitro binding assay using radioligand is the most sensitive techniques available to quantitatively determine the binding affinities of compounds to certain proteins. Our previous studies have shown that BMB binds to myelin sheaths with high affinity and specifity (Stankoff, B.; Wang, Y.; Bottlaender, M.; Aigrot, M. S.; Dolle, F. et al. Imaging of CNS myelin by positron-emission tomography. *Proc Natl Acad Sci USA* 2006, 103, 9304-9309). For this reason, tritiated BMB was custom synthesized by American Radiolabeled Chemicals Inc. (St Louis, Mo.) and was used as the radioligand for binding assays. This allowed us to determine the binding affinities of the newly synthesized compounds using isolated rat myelin fractions. Saturation experiment was first conducted using [³H]BMB. As shown in FIG. 3, [³H]BMB displayed saturable binding with isolated myelin fractions of rats and approximately 30% of [³H]BMB binding to isolated rat myelin was displaced by 1.0 µM unlabeled BMB. Transformation of the saturation binding of [³H]BMB to Scatchard plots gave linear plots, suggesting that it involved single population of binding sites (FIG. 3). The dissociation constant (Kd value) was 1.098±0.20 nM and Bmax value was 17.61 pmol/mg under the assay condition, respectively. Competitive binding assays were also conducted using [³H]BMB as radioligand. The stilbene derivatives competed effectively with [³H]BMB binding sites on rat myelin fractions at affinities of low micromole concentrations. As shown in FIG. 4, the Ki values estimated for 3, 6, 7 and 9 were 370 nM, 119 nM, 126 nM and 494 nM, respectively. These Ki values suggested that all these derivatives of stilbene had relatively high binding affinity for myelin fractions in the order of 7>6>3>9.

In Vitro Staining of Myelinated White Matter

Figure 5:
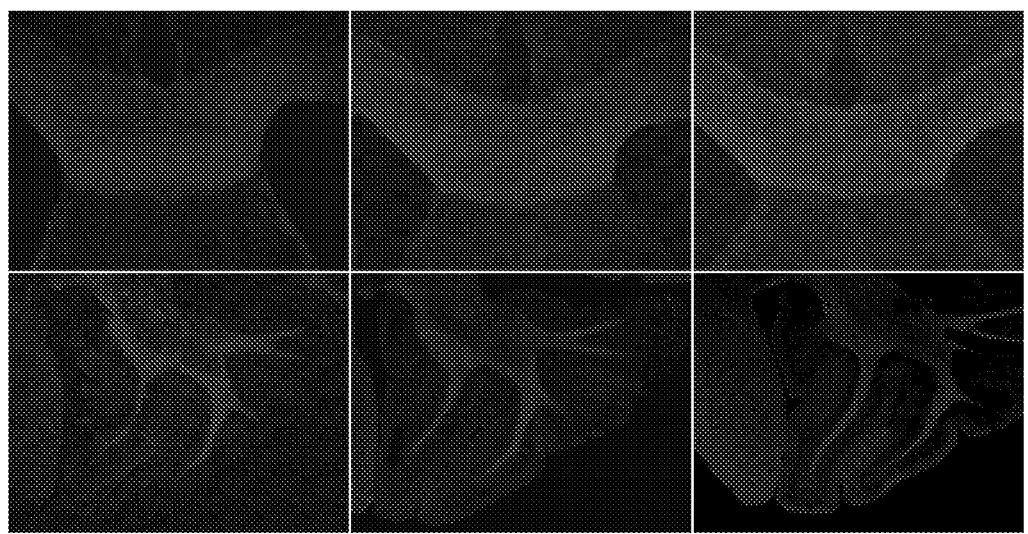
FIG. 5 illustrates photographs of in vitro staining of corpus callosum (top) and cerebellum (bottom) in wild-type mouse brain.

We then evaluated the myelin-binding properties of the newly synthesized compounds 3, 6, and 7 through in vitro staining of mouse brain tissue sections. Both myelinated corpus callosum and cerebellar regions were then examined by fluorescent microscopy. At 10 µM concentration, compounds 3, 6, and 7 selectively labeled both corpus callosum and cerebellum (FIG. 5), exhibiting a staining pattern that were virtually identical to the pattern observed in immunohistochemical staining of MBP (Wu, C.; Tian, D.; Feng, Y.; Polak, P.; Wei, J. et al. A novel fluorescent probe that is brain permeable and selectively binds to myelin. *J Histochem Cytochem* 2006, 54, 997-1004).

In Situ Tissue Staining of Myelinated White Matter

Figure 6:
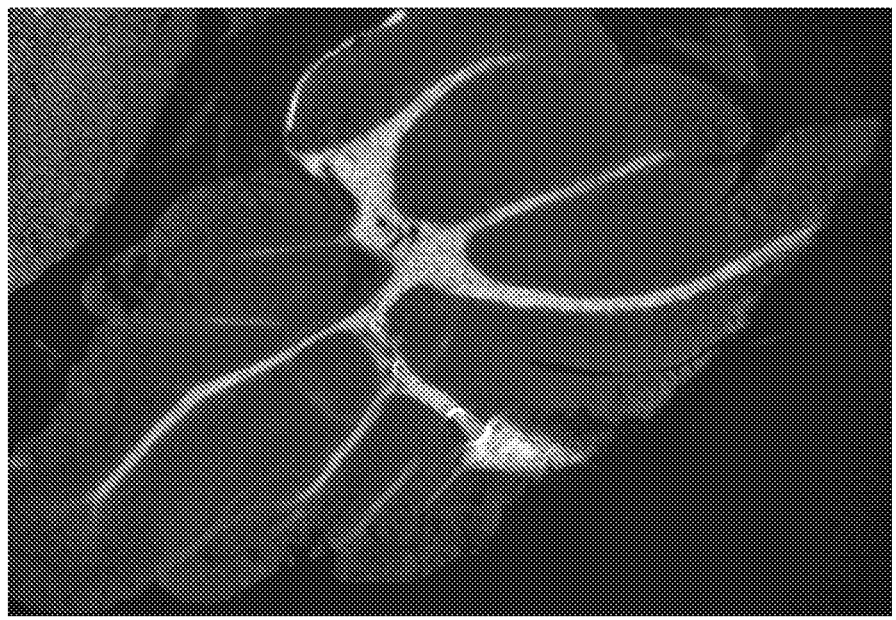
FIG. 6 illustrates photographs of in situ staining of myelin sheaths in the cerebellum of mouse brain.
Figure 6:

Following our in vitro tissue staining studies, we then evaluated the brain permeability and subsequent myelin-binding properties of 6 and 7 in the mouse brain. A dose of 6 or 7 (20-80 mg/kg) was administered via tail vein injection into wild-type mice. Three hours post injection, the mouse brains were perfused with saline followed by 4% paraformaldehyde (PFA) and removed. The fresh frozen brains were then sectioned. Fluorescent staining of myelinated regions such as the cerebellum were then directly examined under a microscope. As shown in FIG. 6, fluorescent compounds 6 and 7 readily entered the mouse brain and selectively labeled myelinated cerebellum.

Partition Coefficient

The partition coefficient (PC) is an important parameter of brain permeability. PC values ranging 1.0~3.5 often show good initial brain entry following i.v. injection (Wu, C.; Pike, V. W.; Wang, Y. Amyloid imaging: from benchtop to bedside. *Curr Top Dev Biol* 2005, 70, 171-213; Levin, V. A. Relationship of octanol/water partition coefficient and molecular weight to rat brain capillary permeability. *J Med Chem* 1980, 23, 682-684; Dishino, D. D.; Welch, M. J.; Kilbourn, M. R.; Raichle, M. E. Relationship between lipophilicity and brain extraction of C-11-labeled radiopharmaceuticals. *J Nucl Med* 1983, 24, 1030-1038. For this reason, we radioiodinated Compound 9 and quantitatively determined the lipophilicity of [¹²⁵I]9. Based on the conventional octanol-water partition measurement, the log Poct of [¹²⁵I]9 was determined as 2.5±0.1, which falls in the range for optimal brain entry.

Permeability Across the Blood-Brain Barrier in Mice

Encouraged by the aforementioned studies, we further evaluated the permeability of [¹²⁵I]9 across the blood brain barrier. Following bolus tail vein injection of [¹²⁵I]9 (0.2 ml, 0.185 MBq), the radioactivity concentration of [¹²⁵I]9 in the brain was determined at 2, 30, and 60 min post injection. As shown in Table 1, [¹²⁵I]9 displayed rapid brain entry at early time intervals. The initial brain entry was 2.29±0.66% ID/g at 2 min post injection. At 30 min post injection, the brain radioactivity concentration reached its peak level (2.65±0.27% ID/g). The radioactivity concentration slowly decreased to 1.12±0.23% ID/g at 120 min post injection. These results indicated that [¹²⁵I]9 readily entered the brain. Retention of [¹²⁵I]9 at later time points was likely due to binding to myelin membranes as indicated by aforementioned in vitro and in situ staining studies.

TABLE 1

| Organ | 2 min. | 30 min. | 60 min. | 120 min. |
|-------|--------|---------|---------|----------|
| Brain | 2.29 ± 0.66 | 2.65 ± 0.27 | 2.05 ± 0.13 | 1.12 ± 0.23 |

Autoradiography in Mice

Figure 7:
FIG. 7 illustrates film autoradiography of [$^{125}$I] 9 binding to myelinated corpus colllosum and cerebellum in mouse brain sections (sagittal). Arrows show myelinated corpus colllosum (A) and cerebellum (B) labeled by [$^{125}$I]9.

To further evaluate the binding specificity of [¹²⁵I]9 to myelin sheaths in the brain, in vitro autoradiography was carried out in mice. As shown in FIG. 7, a distinct labeling of myelinated regions such as corpus callosum and cerebellum were observed after the mouse brain tissue sections (sagittal) were exposed to [¹²⁵I]9. The result indicated that the autoradiographic visualization was consistent with the histological staining of myelinated regions (i.e. corpus callosum and cerebellum).

Synthesis of Trans-Stilbene Derivatives

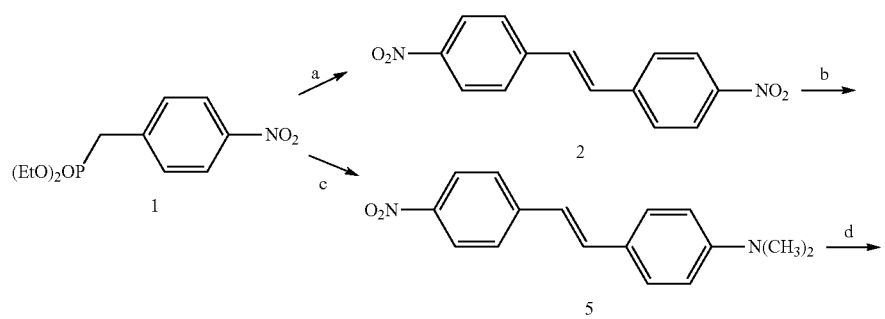

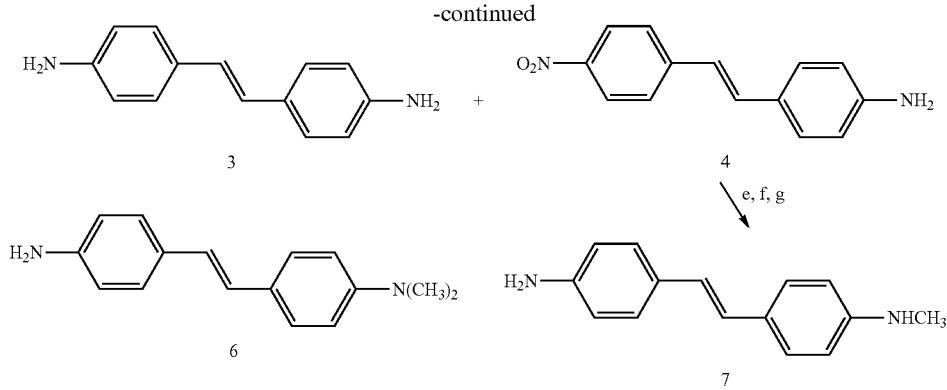

Scheme 1, a) NaH, 4-nitrobenzaldehyde, DMF, MeOH, 83%; b) SnCl$_2$, 1N HCl, THF; c) 4-Dimethylamino-benzaldehyde, DMF, EtOH, NaOCH$_3$, 65%; d) SnCl$_2$, EtOH, 64%; e) (CF$_3$CO)$_2$O, Et$_3$N, THF; f) 1. NaH, MeI, DMF; 2. 1 N NaOH, MeOH; g) SnCl$_2$, CH$_3$COOH, reflux, 35% for 4 steps.

Synthesis of 4,4'-dinitro-trans-stilbene (2)

Under Ar, (4-nitro-benzyl)-phosphoric acid diethyl ester (1, 1.81 g, 6.6 mmol) and 4-nitrobenzaldehyde (1.00 g, 6.6 mmol) were dissolved in DMF (10 mL) and EtOH (10 mL). Then NaOCH$_3$ (2.3 mL, 4.37 M) in MeOH was added and the suspension was stirred for another 3 hours. The solid was filtered and dried in vacuum to give 1.50 g (yield: 83%) of 4,4'-dinitro-trans-stilbene. $^1$H NMR (300 MHz, CDCl$_3$): 8.28 (d, J=8.4 Hz, 4H), 7.94 (d, J=8.4 Hz, 4H), 7.69 (s, 2H).

Synthesis of 4,4'-diamino-trans-stilbene (3) and 4-[2-(4-nitro-phenyl)-vinyl]-phenylamine (4)

To a solution of compound 2 (0.10 g, 0.4 mmol) in THF (20 mL) was added SnCl$_2$ (1.50 g) dissolved in 1N HCl (10 mL). The reaction mixture was stirred overnight at room temperature. The acidic solution was then neutralized using 1N NaOH and extracted with ethyl acetate (3×20 mL). The combined organic phases were washed with water and brine, dried over Na$_2$SO$_4$, and concentrated. Purification with flash column (HE:EA=2:1 to 1:1) yielded 4,4'-diamino-trans-stilbene (3, 0.03 g, 40%) and 4-[2-(4-nitro-phenyl)-vinyl]-phenylamine (4). $^1$H NMR of 3 (300 MHz, CDCl$_3$): 7.31 (d, J=8.4 Hz, 4H), 6.86 (s, 2H), 6.68 (d, J=8.4 Hz, 4H). HR-ESIMS of 3: m/z calcd for C$_{14}$H$_{14}$N$_2$ (M+H$^+$): 211.1230, found 211.1225. Melting point of 3: 206.1~207.3° C. $^1$H NMR of 4 (300 MHz, CDCl$_3$): 8.22 (d, J=8.0 Hz, 2H), 7.59 (d, J=6.86 Hz, 2H), 7.41 (d, J=8.57 Hz, 4H), 7.22 (d, J=17.14 Hz, 1H), 6.97 (d, J=12.57 Hz, 1H), 6.72 (d, J=10 Hz, 2H).

Synthesis of dimethyl-{4-[2-(4-nitro-phenyl)-vinyl]-phenyl}-amine (5)

To a solution of 4-dimethylamino-benzaldehyde (2.24 g, 15 mmol) and (4-nitro-benzyl)-phosphoric acid diethyl ester (1, 4.10 g, 15 mmol) in DMF (20 ml) and EtOH (20 mL) was added to NaOCH$_3$ (1.62 g, 30 mmol). The suspension was stirred and refluxed for 3 hrs. After cooled to room temperature, the precipitate was filtered and washed thoroughly with ethanol to give dimethyl-{4-[2-(4-nitro-phenyl)-vinyl]-phenyl}-amine (5, 2.55 g, 65%) as red solid, 5 was used without further purification.

Synthesis of dimethyl-{4-[2-(4-amino-phenyl)-vinyl]-phenyl}-amine (6)

To a solution of 5 (2.55 g, 9.5 mmol) in EtOH (100 ml) was added to SnCl$_2$ (8.58 g, 38 mmol). The resulting mixture was refluxed for 4 hrs. The solvent was then removed under vacuum and NaOH (2 mol/L, 40 mL) was added to the residue. The crude solid was filtered and suspended in ethyl acetate (200 ml). The precipitates were then filtered to give dimethyl-{4-[2-(4-amino-phenyl)-vinyl]-phenyl}-amine (6, 1.45 g, 64%) as gray solid. $^1$H NMR (300 MHz, CDCl$_3$): 7.40 (d, J=8.62 Hz, 2H), 7.33 (d, J=8.40 Hz, 2H), 6.86 (d, J=5.92 Hz, 2H), 6.76 (d, J=8.34 Hz, 2H), 6.69 (d, J=8.22 Hz, 2H), 2.99 (s, 6H). HR-ESIMS: m/z calcd for C$_{16}$H$_{18}$N$_2$ (M+H$^+$): 239.1543, found 239.1542. Melting point: 167.7~168.5° C.

Synthesis of N-methyl-{4-[2-(4-amino-phenyl)-vinyl]-phenyl}-amine (7)

To a solution of 4 (50 mg, 2 mmol) dissolved in THF (5 mL) under argon was added to Et$_3$N (1 mL). The solution was stirred for 4 hrs. The solvent was evaporated under vacuum and the protected product was then used without further purification.

To the solution of the above protected product dissolved in DMF (5 mL) were added NaH (0.10 g) and iodomethane (1 mL). The vial was sealed and stirred overnight. Then the solution was diluted with methanol (8 mL) and 1M NaOH solution (2 mL). After stirred for another 2 hours, the solution was extracted with ethyl acetate. The combined organic layer was washed with water and brine and dried over Na$_2$SO$_4$. Following concentration, the reduced product was then subsequently used without further purification.

To the suspension of the above compound in acetic acid (10 mL) was added tin (II) chloride (1.0 g). The suspension was heated to reflux for 2 hrs. After concentration, the residue was dissolved in ethyl acetate, washed with 2 N NaOH solution, water, and brine. Dried over Na$_2$SO$_4$, the solution was concentrated and purified by flash column (Hexanes: ethyl acetate=2:1 to 1:1) to give 15 mg of 7 (0.6 mmol, 35% yield for the above three steps). $^1$H NMR (400 MHz, CDCl$_3$): 7.36 (d, J=8.3 Hz, 2H), 7.32 (d, J=8.2 Hz, 2H), 6.87 (AB, J=18.7 Hz, 16.5 Hz, 2H), 6.69 (d, J=8.2 Hz, 2H), 6.62 (d, J=8.3 Hz, 2H), 3.92 (br, 3H), 2.88 (s, 2H).

HR-ESIMS: m/z calcd for $C_{15}H_{16}N_2$ (M+H$^+$): 225.1386, found 225.1385. Melting point: 143.7~144.7° C.

Synthesis of 4-amino-4'-iodostilbene (8)

To a solution of diethyl 4-nitrobenzylphosphate (0.44 g, 1.61 mmol) dissolved in DMF (10 mL) was added NaH (0.07 g, 1.75 mmol). The suspension was stirred for 1 hour followed by addition of 4-iodo-benzaldehyde (0.35 g, 1.51 mmol). The suspension was stirred for another 2 hours. Water was added and the solid was collected by filtration to give 8 (0.40 g, 1.14 mmol, yield: 75%). $^1$H NMR (400 MHz, CDCl$_3$): 8.24 (d, J=8.65 Hz, 2H), 7.88 (d, J=8.68 Hz, 2H), 7.80 (d, J=8.19 Hz, 2H), 7.49 (m, J=8.2 Hz, 4H).

Synthesis of 4-[2-(4-Iodo-phenyl)-vinyl]-phenylamine (9)

To a suspension of Compound 8 (0.20 g, 0.57 mmol) in ethanol (10 mL) was added Tin (II) chloride (1.00 g, 5 mmol) and heated to reflux for 4 hours under argon. The ethanol was evaporated under vacuum. The residue was dissolved in ethyl acetate, washed with 1 N NaOH, water, and brine. Dried over Na$_2$SO$_4$, the solution was concentrated and purified by flash column (Hexanes:ethyla acetate=2:1 to 1:1) to give 9 (0.18 g, quant. yield). $^1$H NMR (400 MHz, CDCl$_3$): 7.66 (d, J=8.25 Hz, 2H), 7.35 (d, J=8.34 Hz, 2H), 7.04 (d, J=15.73 Hz, 1H), 6.71 (d, J=16.26 Hz, 1H), 6.70 (d, J=8.29 Hz, 2H). HR-ESIMS: m/z calcd for $C_{14}H_{12}IN$ (M+H$^+$): 322.0087, found 322.0084. Melting point: 213.4-215.2° C.

Synthesis of 4-[2-(4-Tributylstannanyl-phenyl)-vinyl]-phenylamine (10)

Under Ar, the substrate 9 (0.05 g, 0.15 mmol) was mixed with (Bu$_3$Sn)$_2$ (1 mL), Pd(PPh$_3$)$_4$ (0.02 g) and Et$_3$N (5 mL). The mixture was sealed in a vial and heated to 80° C. for 1 day. The solvent was evaporated in vacuum and the residue was purified by column to give 10 (44 mg, 0.09 mmol, yield: 60%). $^1$H NMR (400 MHz, CDCl$_3$): 7.42 (s, 4H), 7.33 (d, J=7.87 Hz, 2H), 7.03 (d, J=16.18 Hz, 1H), 6.89 (d, J=16.24 Hz, 1H), 6.66 (d, J=8.08 Hz, 2H), 1.55 (m, 6H), 1.34 (m, 6H), 1.05 (t, 6H), 0.89 (t, 9H).

Radiosynthesis of 4-[2-(4-[$^{125}$I]Iodo-phenyl)-vinyl]-phenylamine ([$^{125}$I]9)

To a sealed vial were added 10 (50 µl, 50 µg in 50 µL of ethanol), [I-125] sodium iodide, and 1 N HCl (100 µL). Subsequently, 100 µL of H$_2$O$_2$ (3%, in water) was added via a syringe at room temperature. After 10 min, the iodination reaction was terminated by an addition of saturated NaHSO$_3$, and the resulting solution was neutralized to pH 7-8 by adding a saturated NaHCO$_3$ solution. The mixture was extracted with ethyl acetate (3×1 ml). The combined organic layers were dried over Na$_2$SO$_4$, and the solvent was removed by a stream of dry nitrogen gas. The residue was purified by high performance liquid chromatography (HPLC; C-18 column, acetonitrile: DMGA (5 mM, pH 7.4): 60/40, flow rate: 1 mL/min; retention time: 21 min) to get 18.5 MBq of final pure product with radiochemical purity over 98% and a specific activity near the theoretical limit (80 TBq/mmol). The chemical identity was verified by co-injection of the "cold standard" (nonradioactive compound).

Partition Coefficients

Partition coefficients (PC) were measured by mixing the radioligands with 3 g (3.65 mL) 1-octanol and 3 g (3.0 mL) buffer (pH 7.40, 0.1 M phosphate) in a test tube. The test tube was vortexed for 3 mM at room temperature and then centrifuged (3500 rpm, 5 mM) 1 ml of samples from the 1-octanol and buffer layers were assayed for radioactivity content in a well γcounter. The partition coefficient was determined by calculating the ratio of cpm/g of 1-octanol to that of the buffer. Samples from the 1-octanol layer were repartitioned until consistent partitions of coefficient values were obtained. The measurement was repeated at least three times. PC was 2.5±0.1 at pH 7.40.

Brain Uptake of [$^{125}$I]9

While under anesthesia, 0.1 mL of a saline solution (consisting of saline (2 mL, 9 mg/mL), propylene glycol (2 mL), ethanol (0.7 mL) and HCl (0.3 mL, 0.3 nM))$^{25}$ containing 5 µCi of radioactive tracer, was injected into the tail veins of mice (Swiss-Webster, 2 month old, 2 mice per group). The mice were sacrificed by heart puncture at 2 mM, 30 mM, 60 min and 120 mM post injection under anesthesia. Brains were rapidly removed and weighed, and the brain uptake was expressed as percentage of injection dose per gram organ (% ID/g), which was calculated by a ratio of per gram tissue counts to counts of 1% of the initial dose (100 times diluted aliquots of the injected radioligand) measured at the same time.

In Vitro Autoradiography of [$^{125}$I]9

Mouse brain sections were incubated in [$^{125}$I]9 (20% Ethanol, 4,380,000 cpm/16 ml) for 1 hr. The slides were quickly washed with PBS buffer (10 mM, pH 7.0) 3 times, saturated Li$_2$CO$_3$ in 40% ethanol (2×3 mM), 40% ethanol (2 mM) and H$_2$O (30 sec). After drying by air, the slides were put in a cassette and exposed to film for 44 hrs to obtain images.

In Vitro Tissue Staining of Normal Control Mice Brain Section

Normal control mice were deeply anesthetized and perfused transcardially with saline (10 mL) followed by fixation with 4% PFA in PBS (10 mL, 4° C., pH 7.6). Brain tissues were then removed, postfixed by immersion in 4% PFA overnight, dehydrated in 30% sucrose solution, embedded in freezing compound (OCT, Fisher Scientific, Suwanee, Ga.), cryostat sectioned at 10 µm on a microtome and mounted on superfrost slides (Fisher Scientific). The brain sections were incubated with compound 3, 6 and 7 (10 µM, 1% DMSO in PBS (10 mM, pH 7.0)) for 20 minutes at room temperature in dark. Excess compounds were washed by briefly rinsing the slides in PBS (10 mM, pH 7.0) and coversliped with fluoromount-G mounting media (Vector Laboratories, Burlingame, Calif.). Sections were then examined under a Leica DRMB microscope equipped for fluorescence.

In Situ Tissue Staining of Normal Control Mice Brain Section

Under anesthesia, wild-type mice were injected with compounds 6 and 7 (20-80 mg/kg) via the tail vein, and the mice were then perfused transcardially with saline (10 ml) followed by 4% PFA in PBS (10 ml, 4° C., pH 7.6). Brain tissues were then removed, postfixed by immersion in 4% PFA overnight, dehydrated in 30% sucrose solution, cryostat sectioned at 16 µm on a microtome and mounted on superfrost slides (Fisher Scientific), and imaged directly under fluorescent microscopy without any further staining.

Extraction of Myelin Fractions

Sprague-Dawley (SD) rats were asphyxiated with CO$_2$. When the rat had stopped breathing, the skin/fur over the neck was wetted with a spray of 70% ethanol. The brains were then taken out and put into 0.32 mol/L sucrose (1×Colman buffer) in the homogenizer, first with the loose pestle 5~8 times and then with the tight pestle until the solution reached a uniform consistency. The solution was then transferred from the homogenizer to the corresponding tubes. The tubes were centrifuged at 1000 rpm (4° C.) for 10 minutes. The resulting supernatant was carefully removed and transferred into Beckmann tubes that were previously filled with 2.80 mol/L sucrose and mixed thoroughly. After carefully overlaying nearly to the top of the tube with 0.25 mol/L sucrose, the tube was spun in the Beckman ultracentrifuge for 2.5 hr at 35,000 rpm (4° C.). The 0.25 mol/L sucrose layer was drawn off and discarded. The myelin fraction was collected at 0.25 mol/L and 0.85 mol/L sucrose interface and the pellet was collected at 0.85 mol/L and /1.4 mol/L sucrose interface. Both myelin and pellet were washed with buffer (1×colman, 7~8 mL) three times before suspended in buffer (1×colman, 5 mL) and kept in –80° C. freezer for future use. The concentration of myelin and pellet were determined by Bio-Rad Protein Assay.

Spectrophotometry-Based Binding Assays

In the spectrophotometry-based binding assays, a solution of 6 or 7 (800 μL, 12.5 μM) dissolved in 10% DMSO buffer solution containing 10 mM $MgCl_2$ and 10 mM PBS (pH 7.4) was incubated with isolated myelin or pellets at different concentrations ranging from 0.06 to 14 μg/tube. Each tube contained 10 μM of 6 or 7, 10% DMSO buffer, and membrane fraction in a final volume of 1 mL. Following incubation at room temperature for 1 hr, the free and bound 6 or 7 was separated by centrifugation at 6000 rpm for 10 min The supernatant was then collected and the UV absorption of free 6 or 7 determined by UV spectrometer were at 350 nm or 363 nm. The concentration of free 6 or 7 was obtained by comparison to a standard curve. In parallel, non-specific binding was determined using pellets under the same condition. All assays were performed in triplicate.

Radioligand-Based Binding Assays

The radioligand-based binding assays were carried out in 12×75 mm borosilicate glass tubes. For saturation studies, the reaction mixture contained 50 μL of myelin fraction (1~2 μg, 1×PBS), 50 μL of [$^3$H]BMB (diluted in 1×PBS, 0.25~3.5 nM) in a final volume of 500 μL. Nonspecific binding was defined in the presence of cold BMB (1 μM, diluted in PBS (containing 1% DMSO) in the same assay tubes. For the competition binding, $10^{-5}$ to $10^{-10}$ M compounds and 1.87 nM [$^3$H]BMB were used for the studies. The mixture was incubated at 37° C. for 2 hrs. The bound and free radioactivity were separated by rapid vacuum filtration through Whatman GF/B filters using a Brandel M-24R cell harvester followed by 3×2 mL washes of PBS at room temperature. Filters containing the bound radioligand were dissolved in 6 mL biodegradable counting cocktail overnight and the radioactivity was assayed next day in the scintillation counter (Beckman) with 42% counting efficiency. The results of saturation and inhibition experiments were subjected to nonlinear regression analysis using Graph Pad Prism 4 by which Kd and Ki values were calculated.

Example 2

We screened a series of derivatives based on coumarin that possess the same pharmacophore as stilbene. Coumarin is a naturally occurring compound in plants with many important biological activities. We found that the Coumarin derivitive 3-(4-aminophenyl)-2H-chromen-2-one (CMC), is highly permeable across the BBB and selectively localizes in myelinated regions. Our studies in a hypermyelinated mouse model indicate that CMC is a sensitive probe that can be used for in situ staining of myelin.

Methods and Materials

Figure 9:
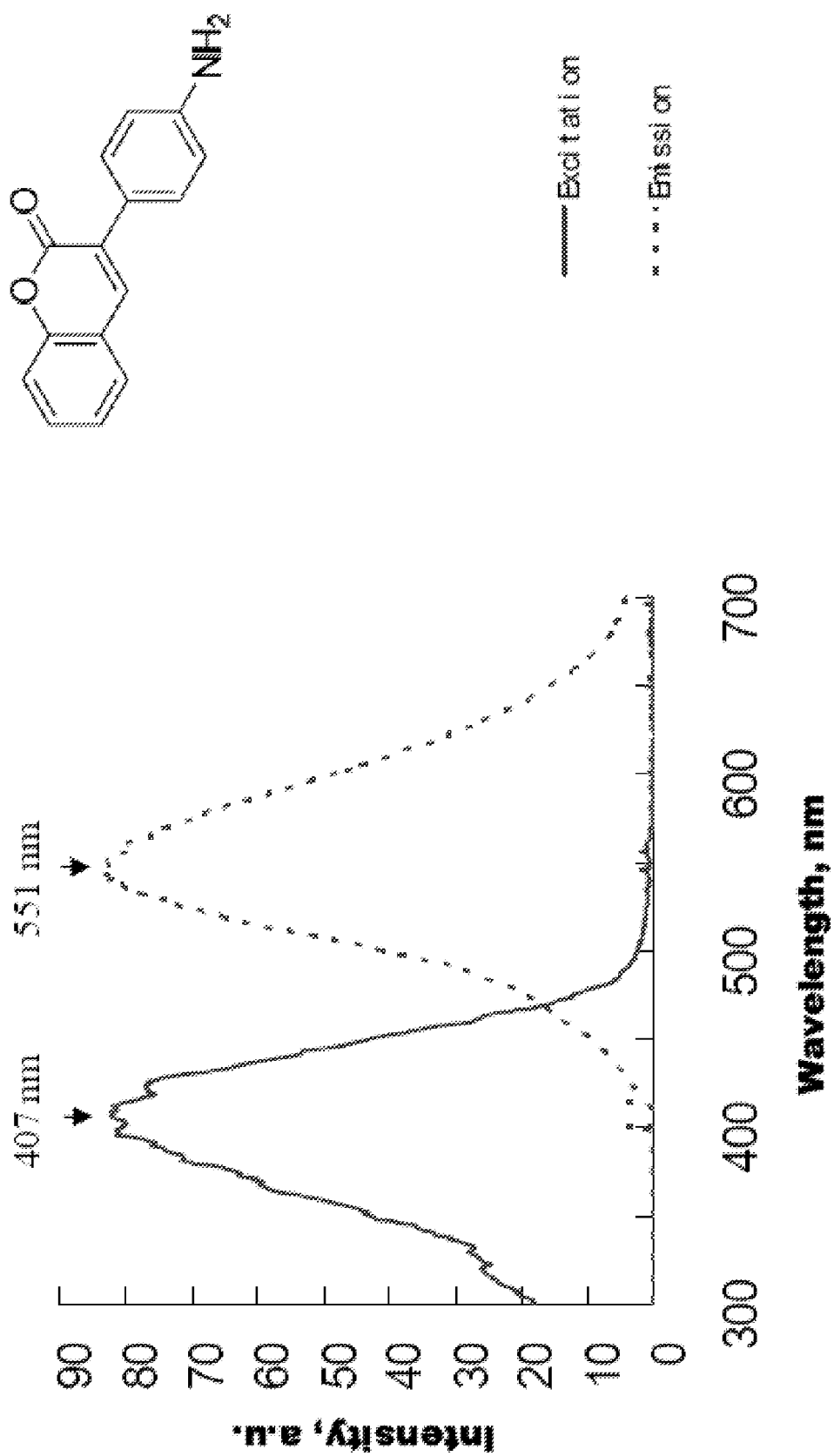
FIG. 9 illustrates Excitation and emission spectra of CMC (10 µM in DMSO). Excitation spectra: emission at 551 nm (range 300-700 nm), maximal excitation wavelength at 407 nm. Emission spectra: excitation at 407 nm (range 300-700 nm), maximal emission wavelength at 551 nm.

Physical and Chemical Properties of Coumarin Derivatives 3-(4-aminophenyl)-2H-chromen-2-one (CMC) was obtained from Matrix Scientific (Columbia, S.C.). The rest of compounds screened were obtained from Sigma-Aldrich (Milwaukee, Wis.), TCI American, (Portland, Oreg.) and used without further purification. The Coumarin derivatives are soluble in DMSO and other commonly used organic solvents. The coumarin derivatives are fluorescent compounds and the excitation and emission spectra of CMC was recorded using Fluorescence Spectrophotometers (Varian. Inc., Palo Alto, Calif.) as shown in FIG. 9.

Animal Preparation

Swiss-Webster R/J mice were obtained from The Jackson Laboratory, Bar Harbor, Minn., and used as control. Transgenic mice expressing constitutively active Akt (HAAkt308D473D, Akt-DD; Ontario Cancer Institute, Toronto, Canada) driven by the Plp promoter (Wight P A, Duchala C S, Readhead C, Macklin W B (1993) A myelin proteolipid protein-LacZ fusion protein is developmentally regulated and targeted to the myelin membrane in transgenic mice. J Cell Biol 123:443-454) were prepared and used as an animal model of hypermyelination. In this model, the Akt cDNA was inserted into the AscI/PacI sites of the modified Plp promoter cassette, and the Plp promoter/Akt-DD insert was injected to generate transgenics in SJL/SWR FI mice to induce hypermyelination. Positive founders were identified by PCR amplification of tail DNA using IntronSV40F (5'-GCAGTGGACCACGGTCAT-3') (SEQ ID NO:1) and Akt lower (5'-CTGGCAACTAGAAGGCACAG-3') (SEQ ID NO:2) primer sequences. Analyses were done from littermatched mice in all developmental experiments, and where possible with older animals.

Immunohistochemistry

For immunohistochemistry, mice were deeply anesthetized and perfused with PBS followed by 4% paraformaldehyde in PBS via the ascending aorta. Brains were dissected out, incubated for 24 hrs in 4% paraformaldehyde at 4° C., cryoprotected and sectioned (30 μm) with a sliding microtome. Sections were immunostained overnight at 4° C. with rabbit anti-MBP antibody (Chemicon-Millipore, Bedford, Mass.) 1:2000 dilution in 3% normal goat serum in PBS, followed by one hour incubation at room temperature with IRDye 800CW Goat Anti-Rabbit (LI-COR Biosciences, Lincoln, Nebr.) 1:5000 dilution. Images of the stained mouse brain sections were acquired on the LI-COR Odyssey infrared imaging system (LI-COR Biosciences, Lincoln, Nebr.).

Tissue Staining

Free floating sections were incubated in 1% $H_2O_2$/Triton-100 for 10 min, then incubated in a solution of test compounds (100 μM) in 1% DMSO/PBS for 30 min at room temperature. The sections were washed three times with PBS before cover-slipping with fluorescence mounting medium (Vectashield, Vector laboratories).

Quantification and Statistical Analysis

Following tissue staining with each test compound, images of mouse brain sections were acquired on a Leica DMI6000 inverted microscope (1.25× and 5× objectives) with a Hamamatsu Orca-ER digital camera, and operated with Improvision's Volocity software. Image J software was used to quantify pixel intensities values. The corpus callosum between the midline and below the apex of the cingulum was defined as region of interest (ROI). The density of myelin in the corpus callosum of wildtype mice was given the arbitrary value of 100, and the density of myelin in Plp-Akt-DD mice was determined as a percentage of wild-type mice. The data were analyzed using the GraphPad Prism, GraphPad Software, La Jolla, Calif., with a nonpaired Student's t test. For correlation, MBP immunoreactivity of the adjacent sections was also determined and quantified on the LI-COR Odyssey infrared imaging system, using 21 μm resolution, 1.2 mm offset with highest quality, and 3.0 channel sensitivity. The integrated densities of the midline corpus callosum were obtained using the associated Odyssey software. Statistical analysis was performed using a non-paired Student's t-test (GraphPad Prism).

In Situ Characterization of CMC

In this experiment, 25 mg/kg of CMC was administered through i.v. injection in the tail vein of 2-month old wild-type mice and Plp-Akt-DD mice Animals were sacrificed at 1 hr after injection through heart puncture. The brains were removed and fixed in 4% PFA. The brains were then sectioned and fluorescent images were directly acquired on a Zeiss Axiovert 200M inverted microscope (2.5× objective) with a AxioCam digital camera (Carl Zeiss MicroImagibg, Inc, Thornwood, N.Y.).

Results

Figure 8:
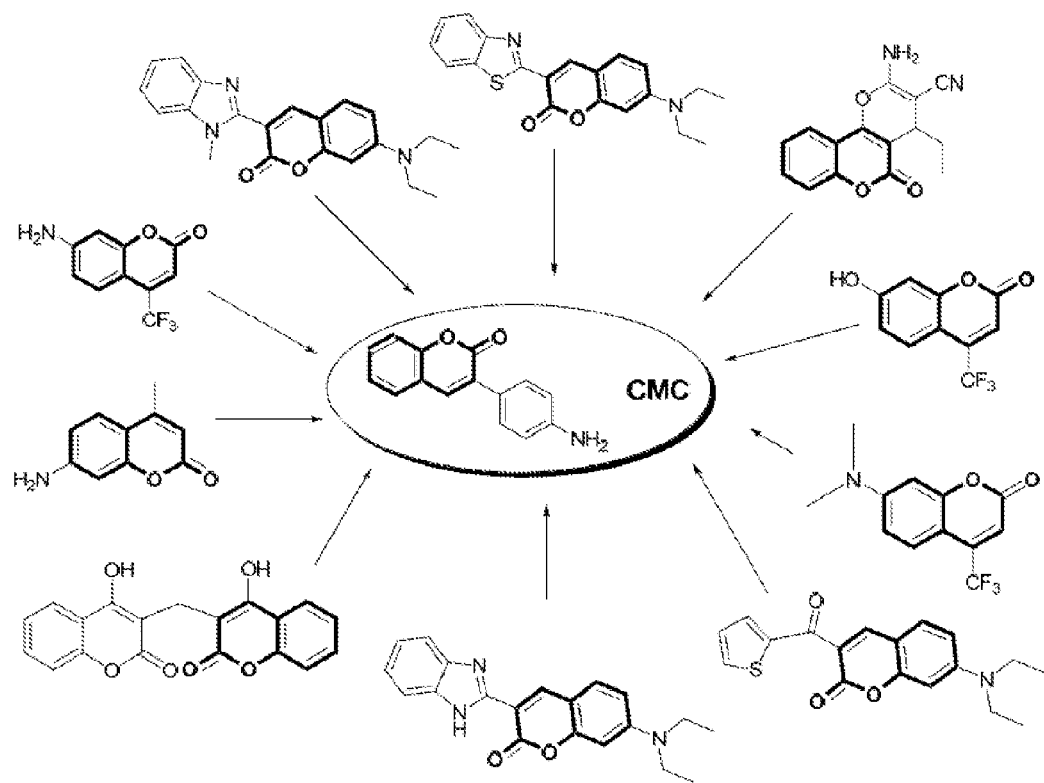
FIG. 8 illustrates structures of coumarin derivatives that have been screened for myelin staining.

To date, we have screened several coumarin derivatives that potentially bind to myelin membranes. The structures of these coumarin derivatives are shown in FIG. 8. All of these compounds are fluorescent and the emission and excitation spectra of CMC are recorded as shown in FIG. 9. The maximal excitation wavelengths were found at 407 nm and the maximal emission wavelengths were found at 551 nm for CMC (Log P 2.68).

In Vitro Tissue Staining

Figure 10:
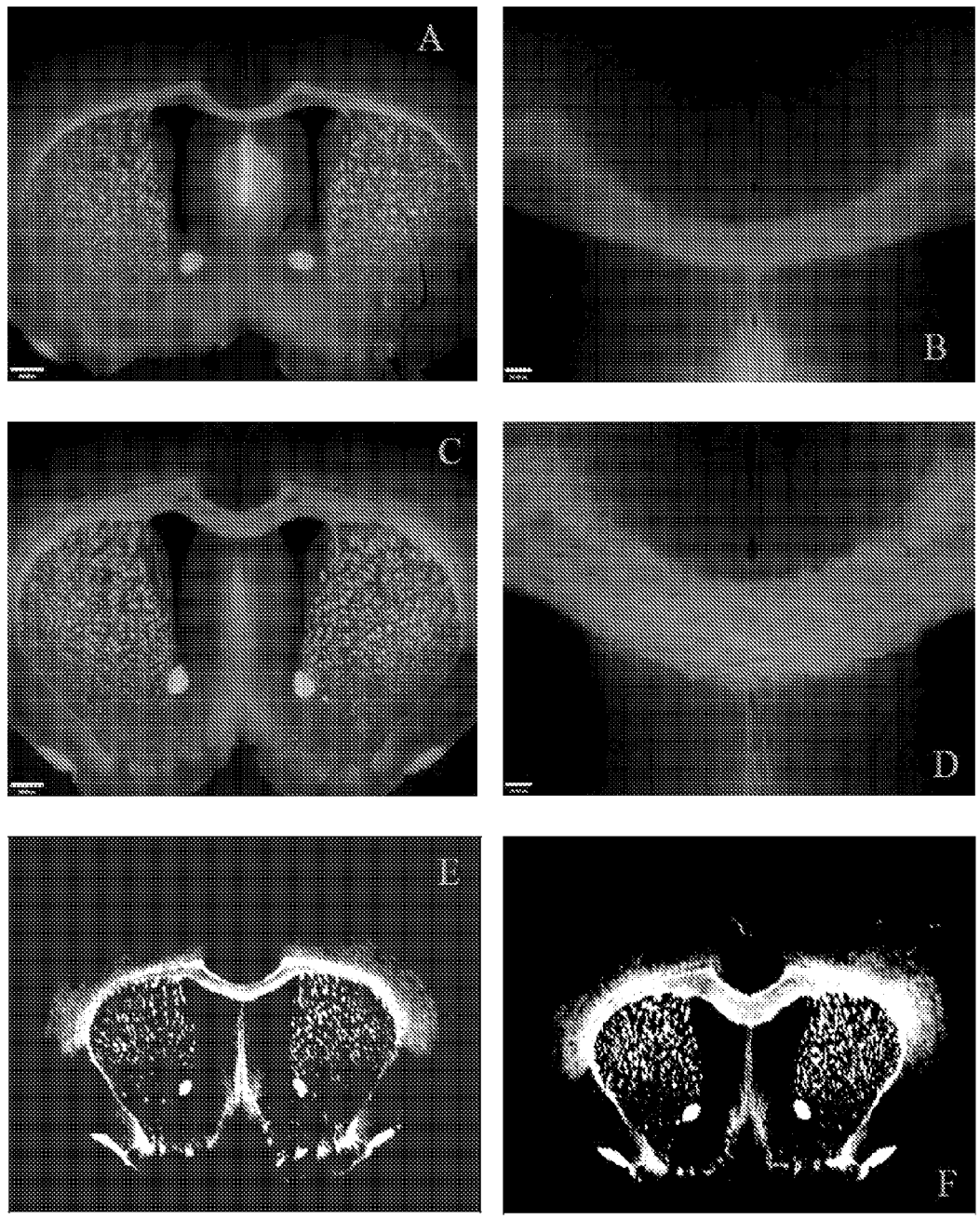
FIG. 10 illustrates in vitro CMC staining of the brain section (A) and corpus callosum (B) in wild-type mouse brain. In vitro CMC staining of the brain section (C) and corpus callosum (D) in Plp-Akt-DD mouse brain. Mbp Immunohistochemical staining of wild-type mouse brain (E) and Plp-Akt-DD mouse brain (F).

The fluorescent nature of these coumarin derivatives allows for staining of mouse brain tissue sections in a way similar to other conventional myelin stains. The tissue staining represents a direct approach to evaluate the binding specificity of the test compounds for myelin sheaths. The myelinated corpus callosum region was then examined by fluorescent microscopy. As shown in FIG. 10, at 100 uM concentration, CMC selectively stained intact myelin tracks in the wild-type mouse brain. Among these coumarin derivaties, CMC shows the highest contrast (FIGS. 10A and B). For correlation, the MBP immunostaining was also conducted in adjacent sections (FIG. 10E).

Figure 11:
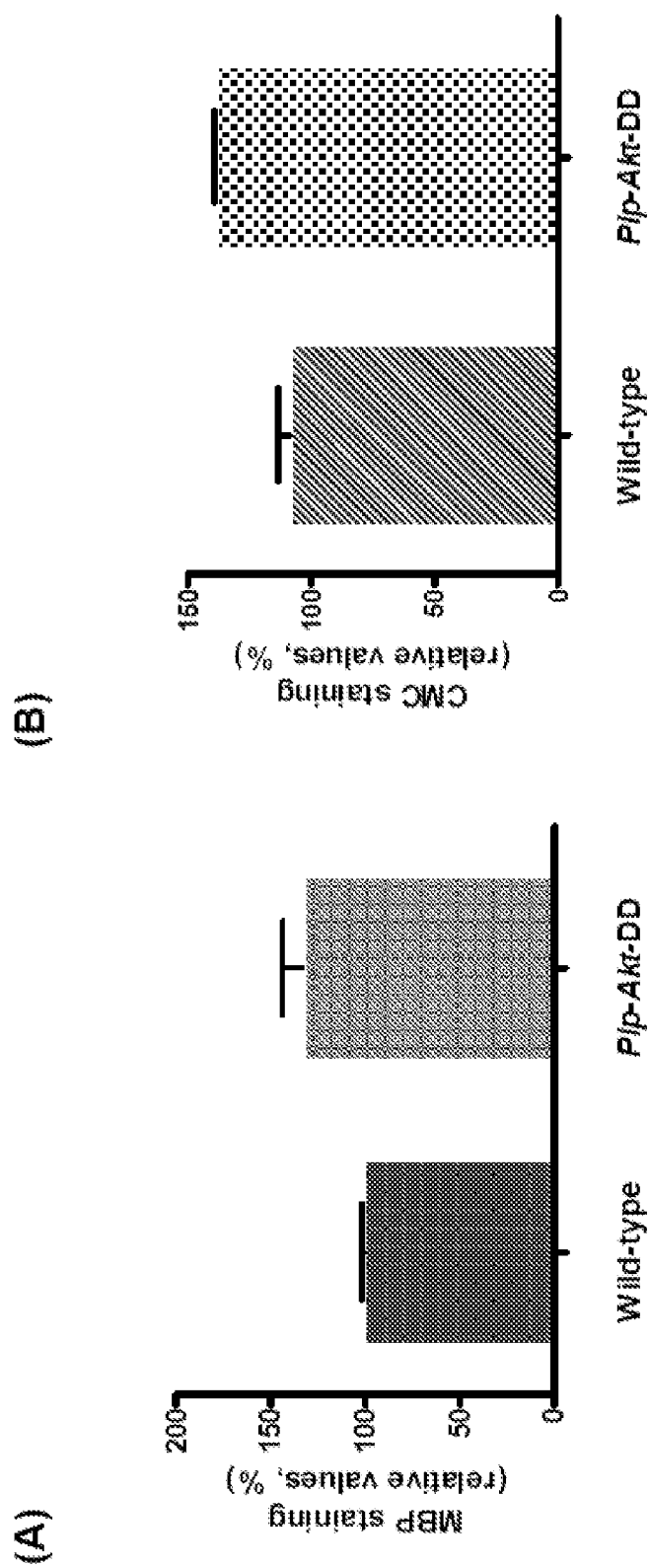
FIG. 11 illustrates quantification of the fluorescent intensity as determined in the same corpus callosum region following MBP staining (A) and chemical staining (B). The data were analyzed using the GraphPad Prism. (A) P=0.0393, n=3, Unpaired t-test; (B) P=0.0393, n=3, Unpaired t-test.

The staining pattern was found consistent with immunohistochemical MBP staining and was proportional to the size of corpus callosum region as demonstrated in a hypermyelinated Plp-Akt-DD mouse model. Compared to the control sections, the hypermyelinated mouse brain showed that the corpus callosum region was significantly enlarged (FIGS. 10C and D). The enlargement was also confirmed by MBP antibody staining using adjacent brain sections (FIG. 11F). Quantitative analysis indicated that the fluorescent intensity is proportional to the level of myelination. As shown in FIG. 11, the MBP antibody staining showed a fluorescent intensity that is 1.31-fold higher in the Plp-Akt-DD model that that in the wild-type control brain. Similarly, CMC staining also exhibited a fluorescent intensity in proportion to the level of myelination. In the Plp-Akt-DD mouse brain, the fluorescent intensity of CMC was found 1.27-fold higher than that in the wild-type mouse brain, which was consistent with MBP immunostaining.

CMC Stains Myelin In Situ

Following our in vitro studies, we investigated the ability of CMC to monitor myelin contents ex vivo in the mouse brain. A dose of 0.5 mg CMC (25 mg/kg) was injected via the tail vein into wild-type mice and Plp-Akt-DD mice. One hr postinjection, mice were perfused and brains were removed and sectioned as described above. CMC staining of myelin was then directly examined under fluorescent microscopy. As shown in FIG. 12, CMC entered the brain and selectively labeled myelin sheaths of the corpus callosum and cerebellum of the wild-type mice and Plp-Akt-DD mice.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, the following is claimed:

1. A method of detecting myelin in vivo in an animal, the method comprising:

(i) administering to the animal a molecular probe including the general formula:

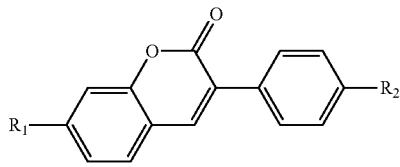

wherein $R_1$ and $R_2$ are each independently selected from the group consisting of H, $NO_2$, $NH_2$, $NHCH_3$, $N(CH_3)_2$, OH, $OCH_3$, $COOCH_3$, SH, $SCH_3$, alkyl derivatives thereof, a halo group, a radiolabel, a chelating group, and a near infrared imaging group or a pharmaceutically acceptable salt thereof;

(ii) detecting the molecular probe in the animal using an in vivo imaging modality to determine myelinated regions in the animal, wherein the detected molecular probe is indicative of myelinated regions of the animal.

2. The method of claim 1, the in vivo imaging modality comprising a Positron Emission Tomography (PET) imaging modality.

3. The method of claim 1, the in vivo imaging modality comprising a micro Positron Emission Tomography (micro-PET) imaging modality.

4. The method of claim 1, further comprising the step of administering the molecular probe to the animal parenterally.

5. The method of claim 1, wherein the molecular probe further comprises a radiolabel.

6. The method of claim 5, the radiolabel including a $^3H$, $^{125}I$, $^{11}C$, or $^{18}F$.

7. The method of claim 1, wherein the molecular probe further comprises a chelating group or a near infrared imaging group.

8. The method of claim 1, wherein $R_1$ and $R_2$ are amines or alkyl derivatives thereof.

9. The method of claim 1, wherein at least one of $R_1$ or $R_2$ is an amine or alkyl derivative thereof.

* * * * *

UNITED STATES PATENT AND TRADEMARK OFFICE
CERTIFICATE OF CORRECTION

| | |
|---|---|
| PATENT NO. | : 9,987,379 B2 |
| APPLICATION NO. | : 13/121742 |
| DATED | : June 5, 2018 |
| INVENTOR(S) | : Yanming Wang and Chunying Wu |

It is certified that error appears in the above-identified patent and that said Letters Patent is hereby corrected as shown below:

In the Specification

Please replace the paragraph in Column 1, after Line 12 with the following:
--GOVERNMENT FUNDING
This invention was made with government support under NS054109 awarded by The National Institutes of Health and W81XWH-10-1-0842 awarded by the department of Defense. The government has certain rights in the invention--

Signed and Sealed this
Twentieth Day of December, 2022

Katherine Kelly Vidal
*Director of the United States Patent and Trademark Office*